US012016764B2

(12) United States Patent
Cartledge et al.

(10) Patent No.: US 12,016,764 B2
(45) Date of Patent: Jun. 25, 2024

(54) TUBULAR IMPLANTS WITH CONTROLLED BIODEGRADATION

(71) Applicant: Poly-Med, Inc., Anderson, SC (US)

(72) Inventors: Jennifer Cartledge, Seneca, SC (US); Kenneth W. Clinkscales, Easley, SC (US); Elizabeth Elvington, Plainview, TX (US); James Hyde, Anderson, SC (US); Brad Johns, Clemson, SC (US); Michael Scott Taylor, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 49 days.

(21) Appl. No.: 16/956,524

(22) PCT Filed: Dec. 21, 2018

(86) PCT No.: PCT/US2018/067372
§ 371 (c)(1),
(2) Date: Jun. 19, 2020

(87) PCT Pub. No.: WO2019/126794
PCT Pub. Date: Jun. 27, 2019

(65) Prior Publication Data
US 2022/0071756 A1 Mar. 10, 2022

Related U.S. Application Data

(60) Provisional application No. 62/610,055, filed on Dec. 22, 2017.

(51) Int. Cl.
*A61F 2/04* (2013.01)
(52) U.S. Cl.
CPC .......... *A61F 2/04* (2013.01); *A61F 2002/048* (2013.01); *A61F 2210/0004* (2013.01);
(Continued)

(58) Field of Classification Search
CPC ................. A61F 2/04; A61F 2002/048; A61F 2210/0004; A61F 2210/0076;
(Continued)

(56) References Cited

U.S. PATENT DOCUMENTS 6,361,558 B1    3/2002   Hieshima et al.
6,368,356 B1 *  4/2002   Zhong ................. A61M 27/008
                                                        523/105

(Continued)

FOREIGN PATENT DOCUMENTS

CN    101257860 A    9/2008
CN    101784243 A    7/2010
(Continued)

OTHER PUBLICATIONS

Supplemental European Search Report, dated Aug. 27, 2021, for European Patent Application No. 18891774.4, a national phase application of PCT Patent Application No. PCT/US2018067372.
(Continued)

*Primary Examiner* — Brian A Dukert
*Assistant Examiner* — Rebecca Lynee Zimmerman
(74) *Attorney, Agent, or Firm* — Meunier Carlin & Curfman LLC

(57) ABSTRACT

Implantable medical devices have zones of high in vivo stability that are adjacent to zones of relatively low in vivo stability, so that when these medical devices are implanted into a host, the zones of low in vivo stability degrade first and allow the formation of independent segments of relatively intact high in vivo stability bands that are sufficiently small that they may pass from the host in a non-harmful manner.

21 Claims, 9 Drawing Sheets

(52) U.S. Cl.
CPC .............. *A61F 2220/0008* (2013.01); *A61F 2230/0091* (2013.01); *A61F 2250/0067* (2013.01)

(58) Field of Classification Search
CPC ........ A61F 2240/001; A61F 2250/0031; A61F 2250/003; A61F 2/88; A61F 2/90; A61F 2/82; A61F 2220/0008; A61F 2230/0091; A61F 2250/0067; A61L 31/10; A61L 31/148; A61L 31/16; A61L 31/14
See application file for complete search history.

(56) References Cited

U.S. PATENT DOCUMENTS

| | | | |
|---|---|---|---|
| 7,794,776 | B1 | 9/2010 | Limon |
| 8,721,519 | B2 | 5/2014 | Sheu et al. |
| 9,005,269 | B2 | 4/2015 | Armstrong et al. |
| 2003/0078649 | A1 | 4/2003 | Camrud et al. |
| 2004/0138738 | A1 | 7/2004 | Stinson |
| 2006/0178739 | A1* | 8/2006 | Shalaby ............... A61M 27/008 623/1.49 |
| 2007/0254012 | A1 | 11/2007 | Luidwig et al. |
| 2007/0282432 | A1* | 12/2007 | Stinson .................... A61L 31/08 148/519 |
| 2008/0004578 | A1 | 1/2008 | Hixon et al. |
| 2008/0071384 | A1 | 3/2008 | Deal |
| 2008/0086199 | A1* | 4/2008 | Dave .......................... A61F 2/82 623/1.42 |
| 2012/0010721 | A1* | 1/2012 | Dillinger .............. A61M 27/008 623/23.7 |
| 2012/0303134 | A1* | 11/2012 | Amos, Jr. ................. A61F 2/82 623/23.66 |

FOREIGN PATENT DOCUMENTS

| | | |
|---|---|---|
| EP | 0947180 | 10/1999 |
| JP | 2006-504487 A | 2/2006 |
| WO | 2004/041345 A1 | 5/2004 |
| WO | 2006/108065 A2 | 10/2006 |
| WO | 2008/130617 A2 | 10/2008 |
| WO | 2016/181371 A1 | 11/2016 |

OTHER PUBLICATIONS

International Search Report and Written Opinion dated Apr. 1, 2019, for International Application No. PCT/US2018/067372.
First Examination Report, dated May 18, 2022, in Indian Patent Application No. 202017030609, filed Dec. 21, 2018, for Applicant Poly-Med, Inc., 6 p.
Office Action, dated Aug. 30, 2022, in Japanese Patent Application No. 2020-534322, filed Dec. 21, 2018, for Applicant Poly-Med, Inc., 2 p.
Office Action, dated Sep. 15, 2022, in Chinese Patent Application No. 201880083213.1, filed 12/21/208, for Application Poly-Med, Inc., 5 p.
Next Generation Biodegradable Ureteral Stent in a Yucatan Pig Model, Ben H. Chew et al, The Journal of Urology, vol. 183, pp. 765-771.
CN Application No. 201880083213.1, Office action dated May 10, 2023.
JP Application No. 2020-534322, Office Action dated Mar. 14, 2023.
JP Application No. 2020-534322, Decision of Rejection dated Sep. 26, 2023.
Re-examination Report received in JP Application No. 2020-534322; dated Feb. 9, 2024; 2 pages.

* cited by examiner

TUBULAR IMPLANTS WITH CONTROLLED BIODEGRADATION

CROSS-REFERENCE TO RELATED APPLICATION

This application is a national phase application under 35 U.S.C. § 371 of International Application No. PCT/US2018/067372, filed Dec. 21, 2018, which claims the benefit under 35 U.S.C. § 119(e) of U.S. Provisional Patent Application No. 62/610,055 filed Dec. 22, 2017; which applications are incorporated herein by reference in their entireties for all purposes.

FIELD OF THE INVENTION

The present invention relates generally to biodegradable medical implants and the manufacture and uses thereof

BACKGROUND

Some medical implants are only necessarily present in a host for a limited period of time. After that period of time has elapsed, the implant may be physically removed, although that often requires additional medical intervention. Alternatively, the implant may be left in place indefinitely. This option is satisfactory in those cases where the long-term presence of the implant is not harmful. As another alternative, the implant may be formed from a bioabsorbable material. A bioabsorbable material will degrade and/or absorb within the host and the components and metabolites thereof will eventually be excreted. Bioabsorable implants are increasingly desired by health care providers, however those implants sometimes cause undesired results, e.g., the host does not tolerate the degradation products.

There is a need in the art for medical implants that do not cause harm to the host as they degrade, compared to existing products. The present invention is directed to fulfilling that need.

SUMMARY

The present disclosure is directed, in one aspect, to medical implants that degrade within a host, where that degradation is managed to occur in a particularly desirable manner due to physical or chemical features that are incorporated into the implant. Implantable medical devices of the present disclosure have zones of relatively high in vivo stability that are adjacent to zones of relatively low in vivo stability, so that when these medical devices are implanted into a host, the zones of low in vivo stability degrade first and allow the formation of independent segments of relatively intact high in vivo stability bands that are sufficiently small that they may pass from the host in a non-harmful manner. A band of low in vivo stability is considered to have low in vivo stability relative to a band of higher in vivo stability that is also present in the medical device. Thus, low and high are meant to be interpreted as relative to one another, where a zone of low in vivo stability has lower in vivo stability than a band of high in vivo stability. A band or zone of low in vivo stability will degrade more quickly than a band or zone of high in vivo stability.

For example, in one embodiment the medical implant comprises a generally tubular hollow structure defined by a having a longitudinal axis that runs along the middle of the lumen of the generally tubular structure and a sidewall that defines the lumen of the structure. This tubular structure comprises a plurality of bands, which may also be called rings or zones or circular strips, that each encircle the longitudinal axis. The plurality of bands comprises relatively high in vivo stability (HIVS) bands that are separated from one another by relatively low in vivo stability (LIVS) bands. The low in vivo stability bands will degrade more quickly when the implant is implanted into a host compared to the relatively high in vivo stability bands. Two LIVS bands may be positioned on either side of a HIVS band, so that when the implant is placed into a host, the two LIVS bands will degrade first and leave behind the intervening HIVS band.

Generally tubular structures of the present disclosure may be designated as -(LIVS-HIVS)n-LIVS-. Alternatively, the generally tubular structure may be designated as -(HIVS-LVS)n-HVS-. In either case, n designates the number of LIVS-HIVS repeating units, and may be an integer of at least 1, up to about 100. Optionally, n is selected from 1, 2, 3, 4, 5, 6, 7, 8, 9, or 10. Optionally, n is selected from 2, 3, 4, 5, 6, 7, 8, 9, or 10. Optionally, n is selected from 3, 4, 5, 6, 7, 8, 9, or 10. Optionally, n is selected from 4, 5, 6, 7, 8, 9, or 10. The medical implant may, and often will, comprise other features besides a generally tubular hollow structure, that render it useful for the intended purpose.

Thus, generally tubular structure of the present disclosure may comprise a portion designated by HIVS1-LIVS1-HIVS2-LIVS2-HIVS3 or HIVS1-LIVS1-HIVS2-LIVS2-HIVS3-LIVS3-HIVS4, or HIVS1-LIVS1-HIVS2-LIVS2-HIVS3-LIVS3-HIVS4-LIVS4-HIVS5, as three examples. In these designations, LIVS1, LIVS2, LIVS3 and LIVS4 are each low in vivo stability bands, and HIVS1, HIVS2, HIVS3, HIVS4 and HIVS5 are each high in vivo stability bands. When an implant having such a construction is placed into a host, the LIVS1, LIVS2, LIVS3 and LIVS4 bands degrade relatively quickly, leaving the HIVS2 and HIVS3 bands to become free from the medical implant and either degrade or be otherwise eliminated at a later time.

Thus, generally tubular structures of the present disclosure may comprise a portion designated by LIVS1-HIVS1-LIVS2-HIVS2-LIVS3, or LIVS1-HIVS1-LIVS2-HIVS2-LIVS3-HIVS3-LIVS4, or LIVS1-HIVS1-LIVS2-HIVS2-LIVS3-HIVS3-LIVS4-HIVS4-LIVS5, as three examples. In these examples, LIVS1, LIVS2, LIVS3, LIVS4 and LIVS5 are each low in vivo stability bands, while HIVS1, HIVS2, HIVS3, HIVS4 are each high in vivo stability bands. When an implant having such a construction is placed into a host, the LIVS bands degrade relatively quickly, allowing intervening HIVS bands to separate from the medical device and then either completely degrade or be otherwise eliminated from the site of implantation at a later time.

In addition, generally tubular structures of the present disclosure may comprise a portion designated by LIVS1-HIVS1-LIVS2-HIVS2, or LIVS1-HIVS1-LIVS2-HIVS2-LIVS3-HIVS3, or LIVS1-HIVS1-LIVS2-HIVS2-LIVS3-HIVS3-LIVS4-HIVS4, as three examples. In these examples, LIVS1, LIVS2, LIVS3, and LIVS4 are each low in vivo stability bands, while HIVS1, HIVS2, HIVS3, HIVS4 are each high in vivo stability bands. When an implant having such a construction is placed into a host, the LIVS bands degrade relatively quickly, allowing intervening HIVS bands to separate from the medical device and then either completely degrade or be otherwise eliminated from the site of implantation at a later time.

When a tubular structure of the present disclosure having alternating HIVS and LIVS bands is placed into a host, the degradation of the implant is, in part, predetermined by specifying the length of the HIVS bands (length being defined as the distance running along the longitudinal axis of the structure, where this may also be referred to as the width of the band) that are separated by LIVS bands. If it is desired that the degradation products of the implant be no longer than, e.g., 5 cm, then the structure may incorporate a plurality of HIVS bands of length equal to or less than 5 cm, each HIVS band flanked by a LIVS band that will also be of less than 1 cm in length. For instance, the LIVS bands may be only 1 cm, or 0.5 cm in length, and the HIVS bands may each be 4 cm of length.

For another example, in one embodiment the medical implant comprises a generally tubular hollow structure defined by a having a longitudinal axis that runs along the middle of the lumen of the generally tubular structure and a sidewall that defines the lumen of the structure. This tubular structure may be further described as having a proximal end and a distal end. In this example, one end (either the proximal or the distal end) degrades more quickly in vivo than does the other end. With this construction, one end may effectively be anchored in place while the other end degrades. Such a construction may incorporate the LIVS and HIVS bands as described previously. For instance, if the implant has a structure comprising proximal end-HIVS1-LIVS1-HIVS2-LIVS2-HIVS3-LIVS3-HIVS4-distal end, LIVS3 may degrade first, followed by degradation of LIVS2, whereupon HIVS3 separates from the implant, and thereafter LIVS1 degrades, whereupon HIVS2 separates from the implant. With this construction, the proximal end of the implant stays implanted longer than the distal end, and additionally, the lengths of the HIVS bands may be controlled. Such a construction may be useful, for example, when the implant is a urethral stent and the proximal end of the implant is inserted into a kidney.

In another embodiment, the proximal end of a medical implant that comprises a generally tubular hollow structure defined by a having a longitudinal axis that runs along the middle of the lumen of the generally tubular structure and a sidewall that defines the lumen of the structure, has a coating, or additional coating, not present on the distal end of the implant. The coating, or additional coating, is resistant to biodegradation and accordingly impedes the in vivo degradation of the implant. For example, the implant may be a urethral stent, where the proximal end of the stent, which is the end that is inserted into the kidney of the host, has a coating, or additional coating, not present on the distal end of the implant. In this way, the proximal end degrades more slowly in vivo than does the distal end of the stent. This is an example of a device of the present disclosure having a compositional vector, which means that the composition of the implant will vary along a dimension of the implant, e.g., more coating may be present on the proximal end of the implant than on the distal end. The coating, or additional coating, may be in addition to the presence of HIVS and LIVS bands that are present in the medical implant, where the HIVS and LIVS bands may be selected to achieve preferential degradation at one end of the implant compared to the other end (another approach to achieving a compositional vector).

In one embodiment, the HIVS and LIVS bands do not provide any functional benefit to the device, e.g., the bands do not make the device stronger or function any better, but are present solely to influence the degradation profile of the implant.

In one embodiment, a generally tubular structure is formed and thereafter the structure is treated to partially modify the structure so as to create one or more HIVS and/or LIVS bands. For example, a structure which inherently has a certain in vivo stability will be treated by methods as disclosed herein, e.g., base or UV treatment, so that the treated portions (e.g., bands) of the structure are converted to lower in vivo stability portions, i.e., portions that have lower stability (faster degradation) when the structure is placed or implanted into a host, such as a stent is implanted into a person, relative to the in vivo stability of the portions/bands of the structure that were not been treated to modify their degradation rate. For example, specific bands of a generally tubular structure may be exposed to degradation conditions to create low in vivo stability (LIVS) bands. Exemplary treatment conditions to create LIVS bands are exposure to basic conditions, i.e., aqueous conditions of high pH, and exposure to radiation, e.g., ultraviolet radiation. Only certain bands of the generally tubular structure are exposed to these degradation conditions, so that the exposed bands are LIVS bands, and the unexposed bands are HIVS bands. For example, turning to the coil (10) of FIG. 6A, bands A, C and E may be exposed to degradation conditions, creating LIVS bands at positions A, C and E, while bands B, D and F are not exposed to degradation conditions, thus creating HIVS bands at positions B, D and E.

The treatment conditions may create LIVS bands, as explained above, or may create HIVS bands. For example, and again turning to coil (10) in FIG. 6A for illustrative purposes, a protective coating may be applied to selected regions to mitigate the rate of coil (10) degradation. Thus, a protective coating may be applied to bands A, C and E, creating HIVS bands at positions A, C and E, and providing LIVS bands at positions B, D and F.

Optionally, the implant may include a containment layer that surrounds part of the implant, where that containment layer is constructed in such a way that the implant degrades in a different manner than it would degrade absent the presence of the containment layer. Also optionally, the implant may include a compositional inhomogeneity where the site(s) of the inhomogeneity are either more or less susceptible to degradation than are the neighboring homogeneous sites of the implant. For instance, the implant may include particles dispersed in a polymer, where the polymer is homogeneous and the particles provides an inhomogeneity that is more susceptible to degradation than is the polymer, or acts as an initiation site for degradation of the polymer. Optionally, the medical device and/or the generally tubular structure does not include a containment layer that restricts the movement of fragments formed during in vivo degradation of the generally tubular structure.

In another embodiment, the present disclosure provides a method of preparing a medical device. The method comprises providing a bioabsorbable medical device, where the bioabsorbable medical device comprises a generally tubular structure with a lumen running down the middle of the generally tubular structure and within a side wall of the generally tubular structure. In other words, a hollow generally tubular structure, such as a stent. The bioabsorbable medical device may optionally be prepared from biodegradable polyester. Bands along the generally tubular structure of the provided medical device are exposed to ex vivo degradation condition to create low in vivo stability (LIVS) bands from the exposed bands. In addition, bands that are adjacent to the exposed bands are not exposed to the same ex vivo degradation conditions, and thus become high in vivo stability (HIVS) bands that are adjacent to the LIVS bands. The present disclosure also provides medical devices prepared by this process and other processes described herein.

In each of the foregoing aspects and embodiments, the generally tubular structure may be a stent, e.g., a ureteral stent. The stent, e.g., the ureteral stent, may comprise a central coil, a mesh, and a coating. The central coil may be a monofilament that is in the shape of a coil. The mesh may be placed on and surrounding the central coil. The coating may be located between the coil and the mesh, as well as on surfaces of the mesh.

These are examples of managed degradation according to the present disclosure, whereby medical implants that degrade within a host are constructed in such a way that degradation is managed to occur in a particularly desirable manner due to physical or chemical features that are incorporated into the implant by the construction of the implant.

The present disclosure describes a number of medical devices, where any of the described medical devices may be modified to exhibit managed degradation by means disclosed herein. For example, any of the medical devices may be modified to include a slit, or to have polymeric components that are selectively degraded to have a gradient of molecular weight, to thereby provide a degradation profile for the device which is managed to occur in a particularly desirable manner due to the physical or chemical features that are incorporated into the implant according to the present disclosure.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

Figure 1:
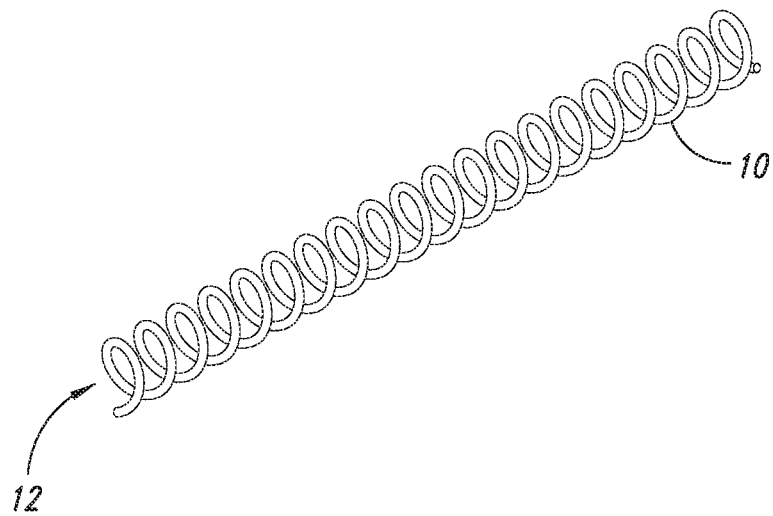
FIG. 1 shows an exemplary generally tubular structure.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art. Any headings used within this document are only being utilized to expedite its review by the reader, and should not be construed as limiting the invention or claims in any manner.

As used throughout this document, including the claims, the singular form "a", "an", and "the" include plural references unless indicated otherwise. For example, "a" polymer includes one or more polymer. As another example, "a" layer refers to one or more layers.

"Degrade" as in a degradable medical device means that the medical device, when placed into a host at a location in the host that is intended for the device, will break down or deteriorate in either a chemical or structural sense. For example, a device that breaks into pieces, e.g., it breaks in half or it disintegrates into many pieces, is a device that has degraded in a structural sense. When the device softens while implanted, then that device also degrades in a structural sense. When some or all of a device dissolves into the biological fluid with which the device is in contact, then that device chemically degrades. Chemical degradation also includes the occurrence of degradation reactions such as hydrolysis, oxidation, and enzymatic bond cleavage. An absorbable or bioabsorbable medical device is a device that will degrade in the host. A degradable implantable medical device refers to an implantable medical device that is intended by the manufacturer and/or the health care provider who recommends the device to have a desirably limited lifetime in the host. In other words, the manufacturer and/or health care provider have made and/or selected the device, in part, because it should naturally degrade in the host and not become a permanent fixture within the host. While degrade includes the situation where complete mass loss occurs, it also includes the situation where partial mass loss occurs, or structural weakening of a location, e.g., a band, of the medical device is caused to occur. For example, a low stability region of a device of the present disclosure may only degrade enough that the mechanical and/or physical properties of the region are compromised such that the region fractures and adjacent regions are no longer in indirect contact with one another.

"Degradation profile" refers to a description of how the implant degrades. The degradation profile may provide a time course for the implant degradation as well as a geometric description of the degradation during the time course. For example, the implant may have a degradation profile whereby the implant degrades along its length from top to bottom over the course of a specified number of days. For example, for a ureter stent of the present disclosure comprising a generally tubular structure with a plurality of HIVS and LIVS bands, the stent may be capable of maintaining patency and remaining at the application site for at least two weeks and is capable of being removed from or repositioned in the ureter as a single piece from the time of implantation to 7 days post implantation. The stent starts to fragment 1-4 weeks following implantation, and the fragments may be excreted. More preferably, the fragmentation can occur between 2 and 3 weeks post implantation. No parts of the stent should remain at the site of application at 5 months. This is an exemplary degradation profile for a medical device of the present disclosure.

"Host" refers to mammals, e.g., humans, dogs, cats, and livestock. The host may also be referred to as a patient or as a subject. A host receives an implantable medical device of the present disclosure.

An implantable medical device as used herein refers to a device such as an instrument or apparatus, intended to be placed or implanted into the body of a host by a heath care provider. The implant may be placed into the host by any suitable manner, e.g., intramuscularly, subcutaneous or intradermally, and may be placed in any suitable location, such as an opening, body lumen or cavity of the host. The medical device provides medical (as opposed to, e.g., purely cosmetic) purposes or benefits, in that it improves the health of the host through any one or more of diagnosing, preventing, treating or curing an undesirable medical condition such as a disease. The medical device may provide a therapeutic benefit. The medical device may provide a prophylactic benefit. The medical device may be an accessory device which does one or more of: supports the performance of a parent medical device by enabling or facilitating that parent device to perform according to its intended use; supplements the performance of a parent device by adding a new function or a new way of using the parent device, without changing the intended use of the parent device; or augments the performance of a parent device by enabling the device to perform its intended use more safely or effectively. The medical device does not achieve its purpose solely through chemical action within the body, and the medical device does not achieve its purpose upon being metabolized.

Figure 2:
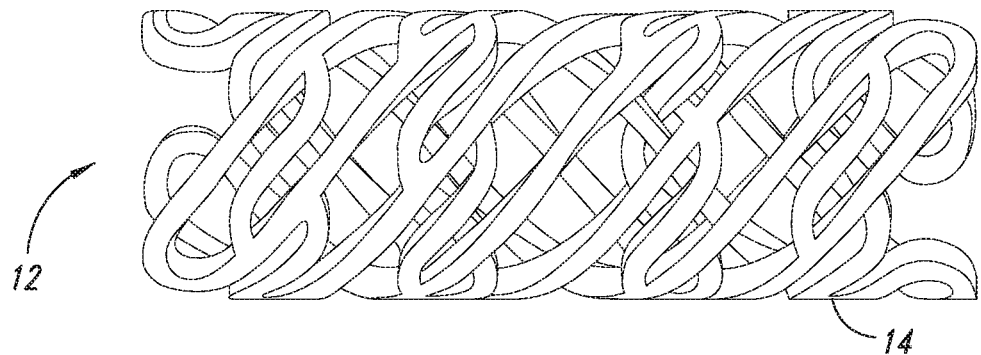
FIG. 2 shows an exemplary generally tubular structure.

The medical devices of the present disclosure include a generally tubular structure as a component of the device. The generally tubular structure may be described as comprising a hollow lumen which runs through the center of the tubular structure, where the hollow lumen is encased by the sidewall of the generally tubular structure. In other words, the medical device includes a pipe-like component. The sidewall of the medical devices of the present disclosure may be solid, like the side wall of a pipe used to carry liquids or gasses. However, unlike a traditional pipe that carries fluids and has a solid impervious sidewall, the generally tubular structures of the present disclosure do not necessarily have a solid sidewall. FIGS. 1 and 2 illustrate exemplary generally tubular structures of the present disclosure which do not have solid, impervious side walls. In FIG. 1, the sidewall is in the shape of a coil (10), so that the generally tubular structure looks somewhat like a spring that includes a lumen (12). In FIG. 2, the side wall is a more complicated mesh-like structure (14) that surrounds a lumen (12). In both of the generally tubular structures of FIG. 1 and FIG. 2, the lumen (12) of the structure can be observed by looking through the side wall (10) or (14), i.e., the side wall has openings so that it is not solid.

Figure 3:
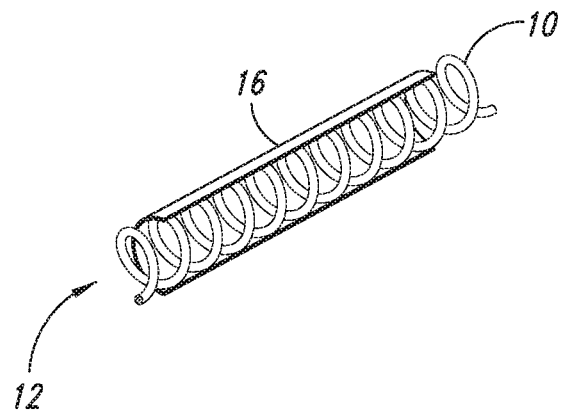
FIG. 3 shows an exemplary generally tubular structure.

The side wall may comprise more than a single component. For example, in FIG. 3, a coil (10) such as illustrated in FIG. 1 is shown having a sheath or blanket (16) wrapped around a portion of the coil (10). In FIG. 3, for illustrative purposes, the blanket (16) is shown as being wrapped around only a portion of the circumference of the coil (10), and such a construction is a generally tubular structure of the present disclosure. However, the blanket (16) may wrapped all the way around the generally tubular structure so that the coil (10) and the lumen (12) are entirely enclosed by the blanket (16). In FIG. 3, the blanket appears solid, i.e., it does not have any holes. However, a blanket such as (16) is not necessarily solid, and may have perforations. In fact, the blanket may be in the form of a mesh that has multiple openings. For illustrative purposes, the blanket (16) is shown in FIG. 3 as being in combination with a coil-like side wall, however according to the present disclosure, a blanket may be in combination any supportive generally tubular side wall configuration, such as the structure (14) shown in FIG. 2.

Figure 4:
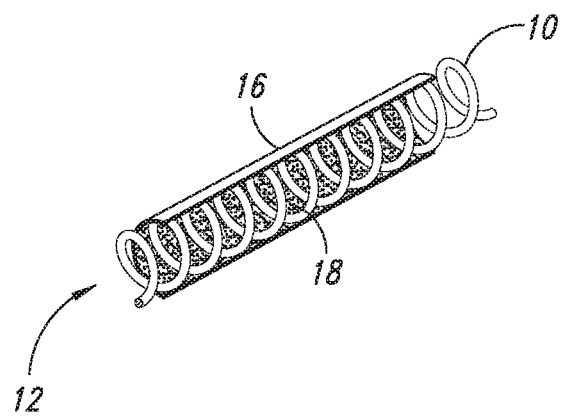
FIG. 4 shows an exemplary generally tubular structure.

Another exemplary side wall component of a generally tubular structure of the present disclosure is a coating. For example, as shown in FIG. 4, the generally tubular structure of FIG. 3, having a coil (10), lumen (12) and a blanket (16) may be, e.g., sprayed with, or dipped into, a solution of organic polymer, so that a coating (18) is deposited on the exterior and/or interior surfaces of the side wall. In FIG. 4, the coating (18) is shown as a darkened surface of the blanket (16) vis-h-vis the equivalent surface of the blanket (16) in FIG. 3 which is uncoated and does not have a darkened surface, and thus as being present on an interior surface of the blanket (16), i.e., the coating (18) is on the surface of the blanket that abuts the coil (10) and faces towards the lumen (12). In general, the sidewall coating may be on and/or within the blanket (16), particularly when the blanket (16) is in the form of a mesh, and the coating is applied by dipping or spraying a coating solution onto the blanket (16). As other examples, the coil (10) of FIG. 1 or the mesh (14) of FIG. 2 may have a coating on some or all of the surface of the structure, so as to provide a side wall that includes a coating.

Thus, the medical devices of the present disclosure will comprise a generally tubular structure having an open lumen that runs essentially through the middle of the structure and is defined by the adjacent side wall. The sidewall may be mono-component, such as shown in FIG. 1 and FIG. 2, or may be multi-component, such as shown in FIG. 3 and FIG. 4.

The structures of the present disclosure are described as being generally tubular to make clear that the invention is not limited to structures that are perfectly symmetrical. The diameter of the lumen may, for example, vary somewhat along the longitudinal axis of the structure. As another example, the generally tubular structure is not necessarily strictly linear, but may bend or curve to some extent. Typically, the generally tubular structure will have a lumen, and that lumen will have an average diameter as determined by the distance between points on the sidewall where that distance passes through the center point of the lumen, and that average diameter will be less than the length of the lumen along a longitudinal axis running from a proximal end to a distal end of the generally tubular structure.

A well-known medical device that comprises a generally tubular structure is a stent, and in one embodiment the medical device of the present disclosure is a stent. Thus, in one aspect, the medical device is a stent that is useful in maintaining or creating patency of a conduit, e.g., a tube or vessel, within a host. Exemplary tubes and vessels are found, for example, along the gastrointestinal (GI) tract of a host, e.g., in the esophagus, the intestine including the transverse colon, the descending colon, the ascending colon, the sigmoid colon and the small intestine, where the small intestine includes the duodenum, the jejunum, and the ileum, the cecum, and the rectum.

In one embodiment the medical implant is designed to be placed in the ureter, i.e., the tube that carries urine from the kidney to the urinary bladder. In another embodiment, the medical implant is designed to be placed in the urethra, i.e., the tube that transports urine from the urinary bladder to outside the host. In another embodiment, the medical implant is designed to be placed into a blood vessel, e.g., the medical implant is a coronary stent or a peripheral stent intended to be placed into a peripheral artery. Other exemplary tubes and vessels are found in organs such as the heart, pancreas, prostate gland, and the kidney. Another location a tube or vessels exists in a host and which may be placed with a medical implant according to the present disclosure is the breast ducts which transport milk from the lobules (milk-producing glands) to the nipple. Other locations for a tubular medical implant include the ear, the tear ducts and the sinuses. Such medical implants are referred to herein as stents.

Figure 5:
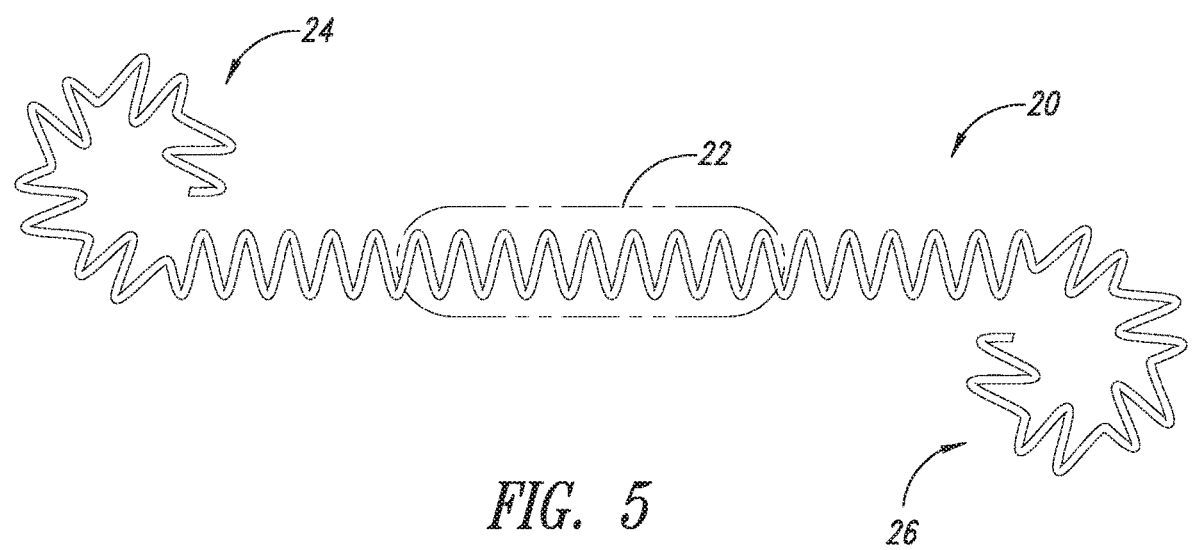
FIG. 5 shows an exemplary medical device incorporating a generally tubular structure.

The generally tubular structure may be a component of a medical device of the present disclosure. For example, as illustrated in FIG. 5, a medical device 20 may include a generally tubular structure identified by the encircled region 22, and also include a proximal end region 24 and a distal end region 26 that may or may not be generally tubular structures. The device 20 is illustrative of a ureteral stent that includes a curled region 24 at the proximal end of the device which may be inserted into the kidney of a host, and a curled region 26 at the distal end of the device which may be inserted into the bladder of a host.

In one aspect, the medical device is formed, at least in part, from one or more of a thermoplastic, thermoset or elastomeric polymer. Optionally, the generally tubular structure is made entirely from polyester, where the term polyester is intended to include one or more polyester polymers. Optionally, the generally tubular structure is made partially from polyester, where the term polyester is intended to include one or more polyester polymers.

In one aspect, the medical device is sterile. Optionally, the medical device is sterilized using gamma radiation or e-beam radiation. In one aspect, the medical device is sterilized using 23-45 kGy gamma radiation. In another aspect, the medical device is sterilized using 25-40 kGy gamma radiation. In yet another aspect, the medical device is placed in a foil pouch which is heat sealed prior to sterilization.

In one aspect, the medical device is intended to be wholly implanted into the host, i.e., to entirely lie under the skin of the host, as opposed to, e.g., a hearing aid that sits in the ear, a dental prosthetic which sits in the mouth of the host, or a contact lens which sits on the eye of a host. In one aspect, the implantable medical device is intended to be placed in a body passageway such as a tube or vessel. Examples of implantable medical devices, which may also be degradable, include stents, shunts, sutures and surgical meshes. Implantable medical devices are also described in the following patent documents: U.S. Pat. Nos. 8,753,387; 8,101,104; 7,594,928; and US 2014/0288636.

Briefly stated, the present invention provides medical implants that exhibit managed degradation after they are implanted into the host. During the process of bioabsorption within a host, the medical device of the present disclosure degrades, i.e., it displays in vivo degradation. In order to manage this degradation process, e.g., to manage the timing of the degradation, the type of degradation, the extent of degradation, and the movement of the degraded medical device including portions thereof within the host, the medical implant may contain a plurality of high in vivo stability (HIVS) bands and low in vivo stability (LIVS) bands. As the name suggests, a HIVS band is relatively more stable in vivo (after implantation) than is a LIVS and.

Figure 6A:
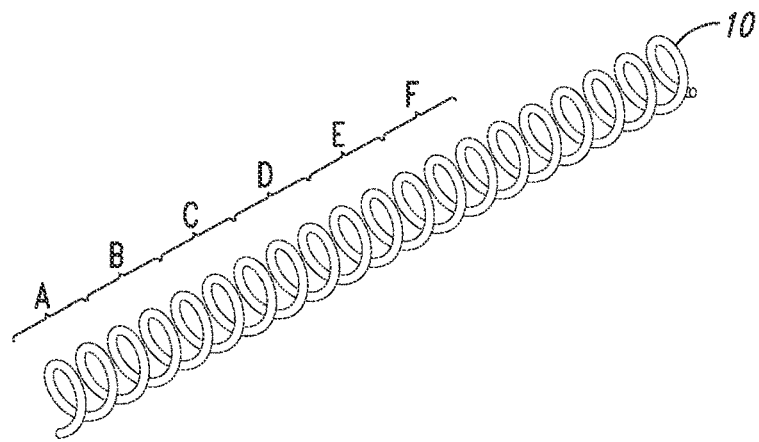
FIG. 6A shows bands A-F of an exemplary generally tubular structure.
Figure 6B:
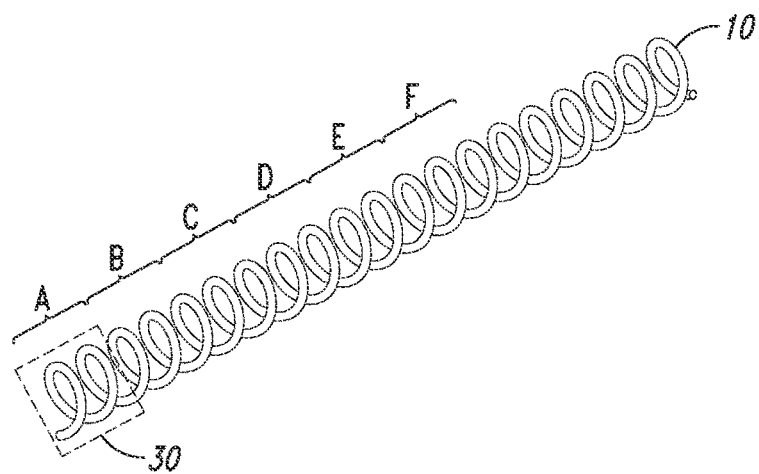
FIG. 6B shows bands A-F of an exemplary generally tubular structure, and specifically highlights band A.

FIG. 6A shows a generally tubular structure in the shape of a coil (10). In FIG. 6A, the generally tubular structure is divided into bands identified as A, B, C, D, E and F. Each of these bands A through F designates a length of the generally tubular structure. In FIG. 6A, the lengths are shown as being equal to one another, however in general, the bands need not be equal to one another in terms of length. To help clarify the portion of coil (10) located within band A, a box (30) formed from dashed lines has been added to the diagram of FIG. 6A to provide the illustration shown in FIG. 6B. As shown in FIG. 6B, band A encompasses approximately the first two coils of the generally tubular structure.

Figure 6C:
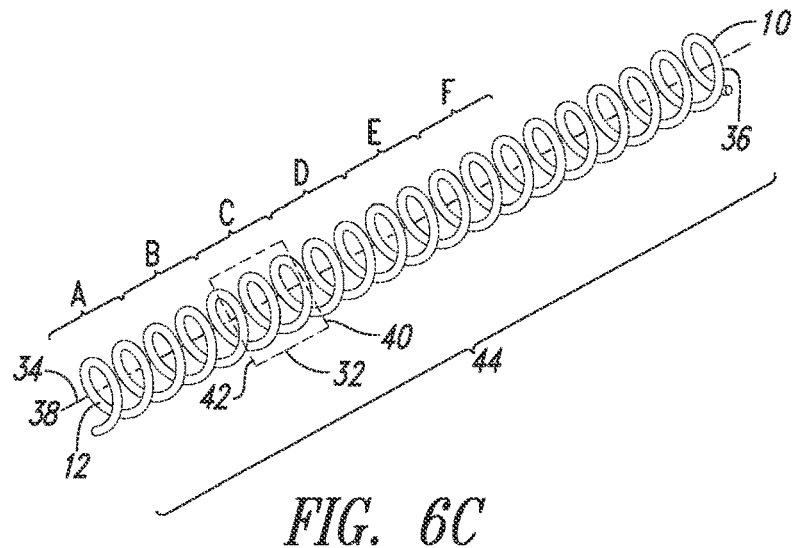
FIG. 6C shows bands A-F of an exemplary generally tubular structure, and specifically highlights band C.

As another illustration of a band structure, FIG. 6C overlays a box (32) on a region of the coil (10) which corresponds to band C of the generally tubular structure depicted in FIG. 6C. Also shown in FIG. 6C is the lumen 12 of the generally tubular structure, through which the longitudinal axis (34) runs from a distal end (36) to a proximal end (38) of the generally tubular structure. The sides of a band, for example the band (32) shown in FIG. 6C, may likewise be characterized in part by having a distal side and a proximal side, for example distal side (40) and proximal side (42) of band C (32) in FIG. 6C. In FIG. 6C, feature (44) refers to the generally tubular structure which comprises the coil (10) that provides the sidewall of the generally tubular structure, and the lumen (12) that runs within the sidewall from a distal end (36) to a proximal end (38) of the generally tubular structure (44). In FIG. 6C, the length of a band, e.g., band C, is measured as the distance between the distal side of the band, e.g., side (40) in FIG. 6C, and the proximal side of the band, e.g., side (42) in FIG. 6C.

In one embodiment, the present disclosure provides a bioabsorbable implantable medical device comprising a generally tubular structure, the generally tubular structure comprising a sidewall enclosing a lumen where a longitudinal axis runs along a length of the lumen from a distal end to a proximal end of the structure. The tubular structure further comprises a plurality of bands that each encircle the longitudinal axis and have a distal side and a proximal side. The plurality of bands include some bands that have relatively high in vivo stability (HIVS), where these HIVS bands are separated from one another by relatively low in vivo stability (LIVS) bands. With this construction, a medical device of the present disclosure will undergo in vivo degradation such that the LIVS bands degrade more quickly than the HIVS bands. This provides an efficient means for the entire tubular structure to degrade since the LIVS bands degrade quickly and leave behind the HIVS bands. The HIVS bands are selected to have a maximum length which is not harmful to the host when these HIVS bands are passed from the conduit where the medical device has been placed. If the HIVS bands are too long, they can get stuck in the host's conduit and this can cause problems until the HIVS bands degrade. But when the HIVS bands are sufficiently short, they readily pass through the conduit even before they have completely degraded, thus facilitating their removal from the host. The HIVS bands are desirably of sufficient length that relatively large portions of the tubular medical device can be excreted from the host even before those portions have completely degraded. With this mechanism, the degradation of a bioabsorbable implant is not entirely dependent on the rate of biodegradation profile of the polymer(s) from which the implant is made. Instead, the implant breaks up into small pieces (each piece being a HIVS band) that can be readily removed from a conduit by the host's natural biological processes, such as fluid flowing through the conduit. In one embodiment, the LIVS bands are selected to have a relatively short length, so that they effectively provide breaks in the generally tubular structure when the device is placed in vivo, and the breaks release bands of HIVS.

The medical devices of the present disclosure may comprise a generally tubular structure that may be designated as proximal end of the tube-(LIVS-HIVS)n-LIVS-distal end of the tube, or proximal end of the tube-(HIVS-LVS)n-HVS-distal end of the tube. In either case, n designates the number of LIVS-HIVS repeating units, and may be an integer of at least 1, up to about 100. Optionally, n is selected from 1, 2, 3, 4, 5, 6, 7, 8, 9, or 10. Optionally, n is selected from 2, 3, 4, 5, 6, 7, 8, 9, or 10. Optionally, n is selected from 3, 4, 5, 6, 7, 8, 9, or 10. Optionally, n is selected from 4, 5, 6, 7, 8, 9, or 10. In this embodiment, the tubular structure comprises alternating bands of relatively high in vivo stability and relatively low in vivo stability. Optionally, the tubular structure comprises a number X LIVS bands, and a number X+1 HIVS bands, so that there is one more HIVS band relative to the number of LIVS bands. In another option, the tubular structure comprises a number Y HIVS bands, and a number Y+1 LIVS bands, so that there is one more LIVS band relative to the number of HIVS bands in the generally tubular structure. Either of X or Y may be selected from 1, 2, 3, 4, 5, 6, 7, 8, 9 or 10 and combinations thereof, e.g., 1, or 2, or 3, or 1, 2, 3 or 4; or 2, 3 or 4, etc.

In some embodiments, the medical device has at least one band of relatively high in vivo stability and also has at least two bands of relatively low in vivo stability. Optionally, the HIVS and LIVS bands alternate along the length of the medical device. For example, optionally, the device has exactly one HIVS band and has exactly two LIVS bands, where one LIVS band is on either side of the HIVS band, i.e., they are present in a construction that may be represented by LIVS-HIVS-LIVS. With this construction, the two LIVS bands degrade relatively quickly, releasing the HIVS band (which has not yet completely degraded, since it has a relatively high in vivo stability compared to the LIVS bands) from the remainder of the medical implant, and allowing the HIVS band to be passed by natural biological action from the host.

In some embodiments, the medical device has at least two bands of relatively high in vivo stability and also has at least one band of relatively low in vivo stability. Optionally, the HIVS and LIVS bands alternate along the length of the medical device. For example, optionally, the device has exactly two HIVS band and has exactly one LIVS band, where one HIVS band is on either side of the LIVS band, i.e., they are present in a construction that may be represented by HIVS-LIVS-HIVS. With this construction, the one LIVS band degrades relatively quickly, releasing the two HIVS bands (which have not yet completely degraded, since they have a relatively high in vivo stability compared to the LIVS band) from the remainder of the medical implant, and allowing the HIVS band to be passed by natural biological action from the host.

In some embodiments, the medical device has at least two bands of relatively high in vivo stability and also has at least three bands of relatively low in vivo stability. Optionally, the HIVS and LIVS bands alternate along the length of the medical device. For example, optionally, the device has exactly two HIVS bands and has exactly three LIVS bands, in a construction that may be represented by LIVS-HIVS-LIVS-HIVS-LIVS. With this construction, the LIVS bands degrade relatively quickly, releasing the HIVS bands from the remainder of the medical implant, and allowing the HIVS bands to be passed by natural biological action from the location within host where the medical device was placed.

In some embodiments, the medical device has at least three ands of relatively high in vivo stability and also has at least four bands of relatively low in vivo stability. Optionally, the HIVS and LIVS bands alternate along the length of the medical device. For example, optionally, the device may have exactly three HIVS bands and exactly four LIVS bands, in a construction that may be represented by LIVS-HIVS-LIVS-HIVS-LIVS-HIVS-LIVS. With this construction, the LIVS bands degrade relatively quickly, releasing the HIVS bands from the remainder of the medical implant, and allowing the HIVS bands to be passed by natural biological action from the location within host where the medical device was placed.

The HIVS and LIVS bands may have specified length, as that dimension is measured along the longitudinal axis of the tubular structure. This dimension may alternatively be referred to as the width of a band, where in this situation, the length and width of a band refer to the same dimension. In one embodiment, the LIVS bands of a medical device of the disclosure have shorter lengths than do the HIVS bands of the medical device. For example, the HIVS bands may be greater than 1 cm in length, or greater than 1.1 cm in length, or greater than 1.2 cm in length, or greater than 1.3 cm in length, or greater than 1.4 cm in length, or greater than 1.5 cm in length, while the LIVS bands are less than 1 cm in length, or less than 0.9 cm in length, or less than 0.8 cm in length, or less than 0.7 cm in length, or less than 0.6 cm in length, or less than 0.5 cm in length. In this way, relatively small LIVS bands degrade relatively quickly, leaving behind relatively large HIVS bands which more slowly degrade and/or are expelled from the conduit in which the device was placed, according to natural mechanisms of the host, e.g., fluid flow through the conduit causes the free HIVS bands (i.e., HIVS bands that are no longer affixed to the medical device) to travel out from the conduit.

Stated another way, in one embodiment the HIVS bands are longer (wider) than the LIVS bands. Thus, the HIVS bands extend further along the longitudinal axis of the tubular structure than do the LIVS bands. For example, in one embodiment the medical device comprises at least two bands of relatively high in vivo stability, each having a width of 1-6 cm, where these bands are separated from one another by a band of relatively low in vivo stability that has a width of less than 1 cm. In this embodiment, the length of the tubular structure is primarily composed of HIVS bands that are separated by LIVS bands. Such a construction may be represented by the designation (LIVS-HIVS)n-LIVS where n represents a number of repeating LIVS-HIVS pairs, where n may be 1, 2, 3, 4, 5, 6, 7, 8, 9 or 10. Optionally, each LIVS band is less than 1 cm, or less than 0.8 cm, or less than 0.6 cm, or less than 0.4 cm, or less than 0.2 cm, or less than 1 cm in width, while the HIVS bands are each at least 1 cm in width.

Optionally, the device has at least two HIVS bands, and each of the HIVS bands has a length of 2-6 cm. A LIVS band is located between two HIVS bands, where the LIVS bands have a length of less than 1 cm. Such a construction may be represented by the designation (LIVS-HIVS)n-LIVS where n represents a number of repeating LIVS-HIVS pairs, where n may be 1, 2, 3, 4, 5, 6, 7, 8, 9 or 10. Optionally, each LIVS band is less than 1 cm, or less than 0.8 cm, or less than 0.6 cm, or less than 0.4 cm, or less than 0.2 cm, or less than 1 cm in width, while the HIVS bands are each at least 1 cm in width.

Optionally, the device has at least two HIVS bands, and each of the HIVS bands has a length of 3-6 cm. A LIVS band is located between two HIVS bands, where the LIVS bands have a length of less than 1 cm. Such a construction may be represented by the designation (LIVS-HIVS)n-LIVS where n represents a number of repeating LIVS-HIVS pairs, where n may be 1, 2, 3, 4, 5, 6, 7, 8, 9 or 10. Optionally, each LIVS band is less than 1 cm, or less than 0.8 cm, or less than 0.6 cm, or less than 0.4 cm, or less than 0.2 cm, or less than 1 cm in width, while the HIVS bands are each at least 1 cm in width.

Optionally, the medical device has at least three bands of relatively high in vivo stability, where each HIVS band has a length 3-6 cm. These three HIVS bands are separated by two bands of relatively low in vivo stability, where each LIVS band has a length of less than 1 cm. Such a structure may be represented by the designation HIVS-LIVS-HIVS-LIVS-HIVS.

Optionally, the medical device has at least three bands of relatively high in vivo stability, where each HIVS band has a length 3-6 cm. In addition, the device has at least four LIVS bands that sit on either side of each of the HIVS bands. Each LIVS band has a width of less than 1 cm. Such a structure may be represented by the designation LIVS-HIVS-LIVS-HIVS-LIVS-HIVS-LIVS.

Optionally, the medical device has at least four bands of relatively high in vivo stability each HIVS band has a length 3-6 cm. These four HIVS bands are separated by three bands of relatively low in vivo stability having a length of less than 1 cm. Such a construction may be represented by the designation HIVS-LIVS-HIVS-LIVS-HIVS-LIVS Optionally, the medical device has at least three bands of relatively high in vivo stability, each having a length of 2-5 cm and being separated by two bands of relatively low in vivo stability, each LIVS band having a length of less than 1 cm. As another option, the medical device has at least three bands of relatively high in vivo stability, each having a length of 3-6 cm and being separated by two bands of relatively low in vivo stability, each LIVS band having a length of less than 1 cm.

In one embodiment, the LIVS bands all degrade more rapidly than do the HIVS bands present in a medical device of the present disclosure. Thus, in one embodiment, the present disclosure provides a medical device comprising a generally tubular structure, wherein the tubular structure comprises at least two bands of relatively high in vivo stability that are separated by one band of relatively low in vivo stability, and where the band of relatively low in vivo stability degrades at least twice as quickly in vivo as compared to the at least one band of relatively high in vivo stability.

Optionally, all of the HIVS bands degrade at essentially the same rate in vivo. Thus, the present disclosure provides a medical device comprising a generally tubular structure, wherein the tubular structure comprises a plurality of bands that have essentially identical relatively high in vivo stability.

Optionally, all of the LIVS bands degrade at essentially the same rate in vivo, so that in vivo degradation of the medical device results in a plurality of independent HIVS bands being formed essentially simultaneously. Thus, the present disclosure provides a medical device comprising a generally tubular structure wherein the tubular structure comprises at least two bands of relatively high in vivo stability that are separated by one band of relatively low in vivo stability, and the at least two bands of relatively high in vivo stability have essentially identical in vivo stability. In addition, the present disclosure provides a medical device comprising a generally tubular structure wherein the tubular structure comprises at least two bands of relatively low in vivo stability that are separated by one band of relatively high in vivo stability, and the at least two bands of relatively low in vivo stability have essentially identical in vivo stability.

However, as another option, the LIVS bands do not all degrade at the same rate. For example, the medical device of the present disclosure may comprise a tubular structure that comprises a band of relatively low in vivo stability located on each side of one band of relatively high in vivo stability, and the two bands of relatively low in vivo stability have non-identical in vivo stabilities. This option may be useful when it is desired that degradation of the medical device occur preferentially from one end of the device compared to the other end. For example, when it is desired that the proximal end of the device degrade sooner than the distal end, a structure comprising proximal end-LIVS1-HIVS1-LIVS2-HIVS2-LIVS3-HIVS3-LIVS4-distal end maybe fabricated. In this case, LIVS1 is designed to degrade more quickly than LIVS2, and LIVS2 is designed to degrade more quickly than LIVS3, and LIVS3 is designed to degrade more quickly than LIVS4. In this situation, LIVS1 degrades first, providing a free end for HIVS1. When LIVS2 degrades, the result is that HIVS1 is completely free from the rest of the medical device, and HIVS1 may be later degraded or expelled from the conduit in which the medical device is placed. Thereafter, LIVS3 degrades, which completely frees HIVS2 from the medical device, allowing HIVS2 to be expelled from the conduit. Thereafter, LIVS4 degrades, which completely frees HIVS3 from the medical device and allows HIVS3 to be expelled from the conduit.

In one embodiment, the present disclosure provides a medical device comprising a generally tubular structure, wherein the tubular structure comprises a first band of relatively low in vivo stability that is located on a distal side of a first band of relatively high in vivo stability, and a second band of relatively low in vivo stability is located on a proximal side of the first band of relatively high in vivo stability, and the first band of relatively low in vivo stability has greater in vivo stability than does the second band of relatively in vivo stability.

In one embodiment, the present disclosure provides a medical device of comprising a generally tubular structure, wherein the tubular structure comprises a plurality of relatively low in vivo stability bands extending from a distal end to a proximal end of the structure and separated by bands of relatively high in vivo stability, wherein the in vivo stability of the plurality of relatively low in vivo stability bands increases from the distal end to the proximal end of the structure.

In one embodiment, a generally tubular structure is formed and thereafter the structure is treated to create one or more HIVS and/or LIVS bands. For example, specific bands of a generally tubular structure may be exposed to degradation conditions to create low in vivo stability (LIVS) bands. Exemplary treatment conditions to create LIVS bands are exposure to basic conditions, i.e., aqueous conditions of high pH, and exposure to radiation, e.g., ultraviolet radiation. Only certain bands of the generally tubular structure are exposed to these degradation conditions, so that the exposed bands become LIVS bands, and the unexposed bands are relatively more stable in vivo, i.e., are HIVS bands. For example, turning to the coil (10) of FIG. 6A, bands A, C and E may be exposed to degradation conditions, creating LIVS bands at positions A, C and E, while bands B, D and F are not exposed to degradation conditions, thus positions B, D and F become HIVS bands. As mentioned previously, LIVS and HIVS are relative terms: high in vivo stability (HIVS) bands are higher in terms of in vivo stability than are low in vivo stability (LIVS) bands.

Figure 7B:
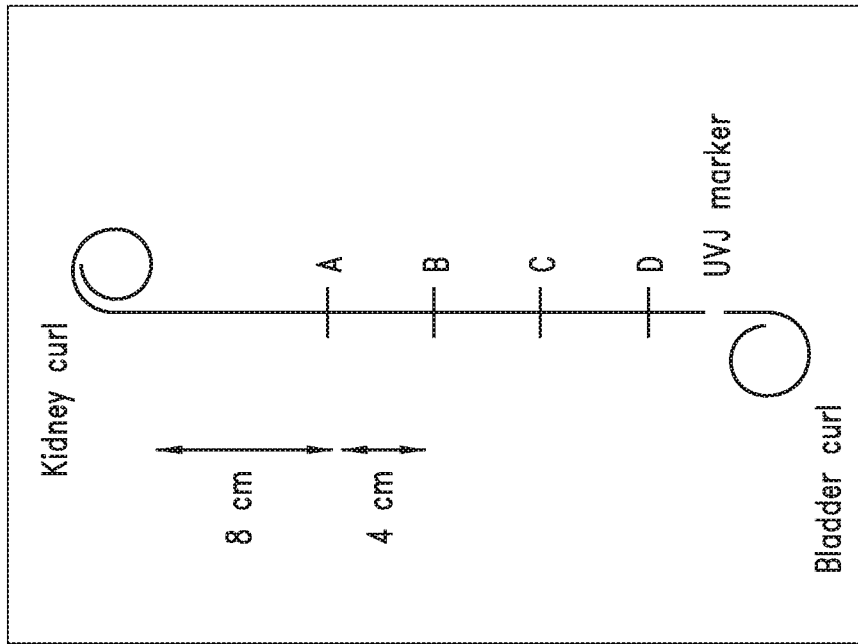
FIG. 7B is a schematic of a medical device of the present disclosure having locations A, B, C and D specified on the generally tubular structure of the medical device.
Figure 7A:
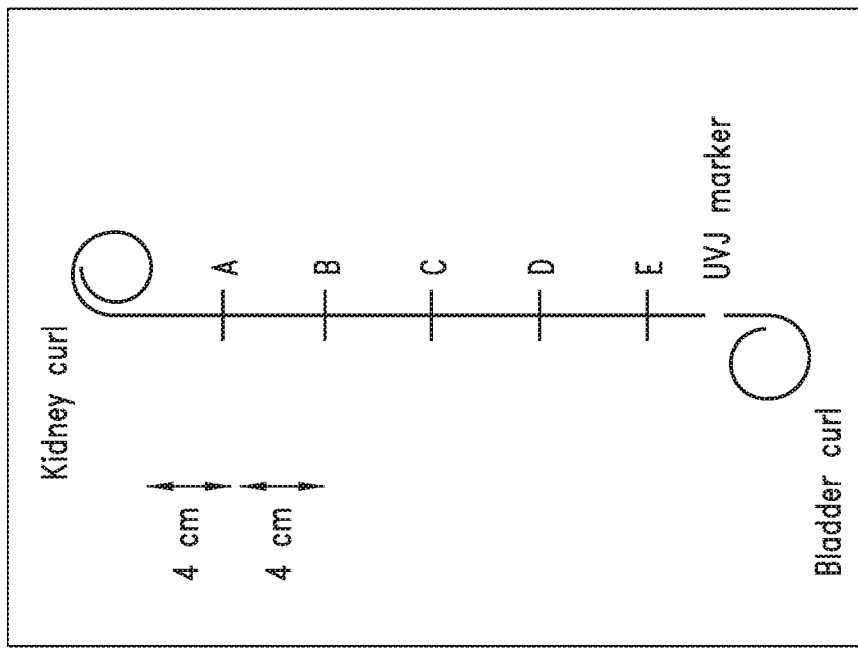
FIG. 7A is a schematic of a medical device of the present disclosure having locations A, B, C, D and E specified on the generally tubular portion of the medical device.

As an illustration of a medical device of the present disclosure, FIG. 7A provides a schematic image of a ureteral stent having a kidney curl at one end which provides a kidney retaining end, and a bladder curl at the other end which provides a bladder retaining end at the other end of the stent. The schematic of FIG. 7A identifies locations A, B, C, D and E on the generally tubular structure located between the kidney curl and the bladder curl. In the schematic, each of locations A, B, C, D and E is the mid-point of a band of approximately 0.1-0.5 cm width, such as a LIVS band. The regions between the bands having mid-points a locations A-E are HIVS bands. To summarize, each of A, B, C, D and E represents the location of a LIVS band, and the regions between A and B, and between B and C, and between C and D, and between D and E each represent the location of an HIVS band. In order to achieve a gradient degradation, the band at location E may be exposed to relatively harsh degradation condition, while the band at location D is exposed to somewhat less harsh degradation conditions, while the band at location C is exposed to even less harsh degradation conditions than were used to create the band at location D. Likewise for the bands at locations B and A. Thus, the band at location A is exposed to the least harsh degradation conditions, and the harshness of the degradation conditions increases in the order A, B, C, D and E. In FIG. 7A, location E may receive, for example, degradation treatment by 1.5 M NaOH, while location D receives degradation treatment by 1.25 M NaOH, while location C receives degradation treatment by 1.0 M NaOH, while location B receives degradation treatment by 0.75 M NaOH, while location A receives degradation treatment by 0.5 M NaOH. The different locations are exposed to the degradation conditions for a constant period of time, with the only difference being the strength of the basic solution to which the bands are exposed. As an alternative, the same strength of base may be used to degrade each band so as to create LIVS bands, but the band at location E is exposed to the base solution for the longest period of time and the band at location A is exposed to the base for the shortest period of time, with intermediate bands being exposed for intermediate periods of time.

Pursuant to this gradient of degradation treatments, the LIVS band at location E degrades most quickly relative to the other bands. After the band at location E degrades to the point of breakage, the HIVS region between locations E and D will still be part of the generally tubular structure. However, of the remaining LIVS bands D-A, the LIVS band at location D is the one that degrades most quickly. Accordingly, the next LIVS band to break will be the LIVS band at location D, thus freeing the HIVS band located between the LIVS bands having midpoints at locations D and E from the medical device. In the absence of a containment layer or equivalent feature, this disassociated HIVS band may be expelled from the body of the host. The LIVS band at location C will degrade more quickly than the LIVS bands at locations B or A, and upon degradation and fracture of the LIVS band at location C, the HIVS band located between positions C and D will become free from the medical device and may be expelled from the body of the host. This gradient of degradation conditions provides for managed degradation of the medical implant in a safe manner, without the need to rely on a containment layer. The fragments that form upon degradation of the generally tubular structure of the medical implant are sufficiently small, due to proper selection of the locations of the LIVS bands, that these disassociated HIVS bands will not cause a health danger to the host as the dissociated HIVS bands are eliminated from the body of the host.

FIG. 7B repeats the schematic shown in FIG. 7A, but illustrates different locations A, B, C and D. In FIG. 7B, a gradient degradation may be created by exposing the bands at locations A, B, C and D to progressively longer times of degradating radiation, e.g., UV radiation. With this approach, the LIVS band at location D will degrade before the LIVS band at location C, while the LIVS band at location B degrades slower than the LIVS band at location C, and the LIVS band at location A degrades most slowly among the bands at locations A, B, C and D. For example, the band at location D may be exposed to UV radiation for 15 seconds, while the band at location C is exposed to the same strength of UV radiation for 12 seconds, while the band at location B is exposed to the UV radiation for 9 seconds, and the band at location A is exposed to the UV radiation for 6 seconds.

In one embodiment, the present disclosure provides a method of preparing a medical device. The method comprises providing a medical device that comprises a bioabsorbable generally tubular structure. Degradating conditions are then applied to at least two bands of the generally tubular structure, to thereby create at least two bands of low in vivo stability (LIVS). One or more bands of high in vivo stability (HIVS) are located between any two LIVS bands. The degradating conditions achieve degradation of the band of the generally tubular structure to which the degrading conditions are applied. The degradating conditions may be, for example aqueous base. Alternatively, the degradating conditions may be UV radiation. The generally tubular structure may be made in whole or part from bioabsorbable polyester where base or UV radiation achieves partial degradation of the polyester.

The treatment conditions may create LIVS bands, as explained above, or may create HIVS bands. For example, and again turning to coil (10) in FIG. 6A for illustrative purposes, a protective coating may be applied to selected regions of a generally tubular structure to mitigate the rate of coil (10) degradation. Thus, a protective coating may be applied to bands A, C and E, creating HIVS bands at positions A, C and E, and thus providing LIVS bands at positions B, D and F. In one embodiment, the coating is a bioabsorbable polyester.

In one embodiment, the present disclosure provides a method of preparing a medical device. The method comprises providing a medical device that comprises a bioabsorbable generally tubular structure. Degradating conditions are then applied to at least two bands of the generally tubular structure, to thereby create at least two bands of low in vivo stability (LIVS). One or more bands of high in vivo stability (HIVS) are located between any two LIVS bands. The degradating conditions achieve degradation of the band of the generally tubular structure to which the degrading conditions are applied. The degradating conditions may be, for example aqueous base. Alternatively, the degradating conditions may be UV radiation. The generally tubular structure may be made in whole or part from bioabsorbable polyester where base or UV radiation achieves partial degradation of the polyester.

The present disclosure also provides a method of preparing a medical device comprising providing a bioabsorbable medical device, where the bioabsorbable medical device comprises a generally tubular structure with a lumen running down the middle of the generally tubular structure and within a side wall of the generally tubular structure. In other words, a hollow generally tubular structure, such as a stent. The bioabsorbable medical device may optionally be prepared from biodegradable polyester. Bands along the generally tubular structure of the provided medical device are exposed to ex vivo degradation condition to create low in vivo stability (LIVS) bands from the exposed bands. In addition, bands that are adjacent to the exposed bands are not exposed to the same ex vivo degradation conditions, and thus become high in vivo stability (HIVS) bands that are adjacent to the LIVS bands. The present disclosure also provides medical devices prepared by this process and other processes described herein.

In one embodiment, the degradative conditions are, or include, UV radiation. UV radiation of suitable strength is applied to a portion of the generally tubular structure in order that the UV radiation impinges on that portion of the generally tubular structure and makes changes in the structure of that portion such that the effected portion undergoes an increased rate of in vivo degradation relative to adjacent portions of the generally tubular structure that have not been exposed to the UV radiation. To achieve selective exposure of the generally tubular structure to UV radiation, bands or other shaped portions are shielded from exposure to the UV radiation, while adjacent bands or other portions are not shielded. Shielding may be accomplished by placing a mask over the generally tubular structure, where the mask has perforations through which the UV radiation can pass and contact the generally tubular structure, but the mask also has radiation-opaque regions through which the UV radiation cannot pass. Shielding may also be accomplished by placing the generally tubular structure within a metal block that has a lumen into which the generally tubular structure may be inserted and sit in a resting position. The metal block may have holes that extend through the metal, i.e., between the outer surface of the metal block and the lumen of the metal block. UV radiation can be directed into the holes from the outer surface of the block, so that the radiation travels through the hole and exits into the lumen of the metal block, whereupon the UV radiation impinges on that portion of the generally tubular structure that is exposed to the UV radiation. By adjusting or selecting the diameter of the hole, the size of the portion of the tubular structure being impinged by the UV radiation is likewise selected. For example, if the hole has a diameter of 5 mm, then the length of the generally tubular structure exposed to UV radiation will likewise be about 5 mm.

The generally tubular structure may or may not have a solid support (e.g., an opaque rod) running down the lumen of the generally tubular structure during the time the structure is exposed to UV radiation. Particularly when an opaque rod runs down the lumen of the generally tubular structure, this rod may block exposure of some portions of the generally tubular structure to the incoming UV radiation. In order to overcome radiation-blockage caused by an opaque solid support, the generally tubular structure may periodically be rotated around its longitudinal axis, so that all portions of a band of the generally tubular structure are exposed to the incoming UV radiation. The rotation may occur constantly, in other words, the generally tubular structure is gradually spun around its longitudinal axis at a constant rate, thereby exposing a band of the structure to UV radiation. Alternatively, the rotation may be performed incrementally, e.g., a portion of the generally tubular structure (i.e., the portion that is next to the hole in the block through which the UV radiation passes) may be exposed to UV radiation for a desired period of time, then the structure is rotated about its longitudinal axis by, e.g., 60 degrees, then the generally tubular structure is again exposed to UV radiation for a desired period of time, and then the structure is rotated in the same direction by another 60 degrees, followed by more exposure to UV radiation, etc., until the generally tubular structure has received six doses of UV radiation and a band of LIVS has been created While the foregoing illustration utilized six UV radiation doses at 60 degree intervals of the stent, other treatment regimens may alternatively be used, e.g., 4 doses applied to a stent that is rotated 90 degrees after each dose, or 3 doses applied to a stent that is rotated 120 degrees after each dose, etc. Also, in addition to rotating the generally tubular structure around its longitudinal axis, the generally tubular structure may be moved along its longitudinal axis, so that a helical pattern of LIVS bands are created.

In order to create a generally tubular structure having multiple bands of LIVS, a row of a plurality of holes may be drilled into the block, e.g., two holes to create two LIVS bands, or three holes to create three LIVS bands, etc. The holes are typically in a line, and spaced apart from one another by the desired length of a HIVS band. As mentioned previously, each hole will have a diameter approximately equal to the desired length of a LIVS band. For example, three holes may be placed in a line, each hole having a diameter of 5 mm, where the hold runs from the outer surface of the block to the inner lumen of the block. The holes may be spaced a distance of 4 cm apart. In this way, a generally tubular structure may be created having a HIVS-LIVS-HIVS-LIVS-HIVS-LIVS-HIVS pattern, where the three LIVS bands each have a length of about 5 mm and the two internal HIVS bands each of a length of about 4 cm, where this structure may be represented by HIVS-LIVS (5 mm)-HIVS (4 cm)-LIVS (5 mm)-HIVS (4 cm)-LIVS (5 mm)-HIVS. When the generally tubular structure includes both of a kidney curl at one terminus and a bladder curl at the other terminus, the structure may be represented by (Bladder Curl-HIVS)-LIVS (5 mm)-HIVS (4 cm)-LIVS (5 mm)-HIVS (4 cm)-LIVS (5 mm)-(HIVS-Kidney Curl).

Rather than create multiple holes in a block, a block may have only a single hole, so that the generally tubular structure is moved through the lumen by a desired distance, in order to expose another band of the structure to UV radiation. For example, after a first LIVS band has been created, the generally tubular structure may be offset by a distance of, e.g., 5 cm, so that a new (second) band of the generally tubular structure can be exposed to the UV radiation that passes through the hole in the metal block, thereby allowing formation of a second LIVS band.

The UV radiation may be generated by standard means. For example, a BLUEWAVE™ 200 UV Spot Lamp (Dymax Corporation, Torrington, CT, USA) or equivalent is a suitable source for the UV radiation. A suitable intensity of UV radiation is about 10 W/cm$^2$, e.g., in the range of about 9-11 W/cm$^2$. A suitable time of exposure of a portion of the generally tubular structure to the UV radiation is about 10-60 seconds, in order for that portion of the generally tubular structure to have a suitably low in vivo stability. Different bands may be exposed to UV radiation for different lengths of time, and/or different light intensities, and/or different numbers of exposures, in order to achieve unique degradation and mechanical properties at different places on the stent, so as to vary the rate of the degradation of the different portions when the generally tubular structure is placed in vivo. For example, to create a generally tubular structure where the band nearest the bladder curl is the first to degrade and the band nearest the kidney curl is the last to degrade, the generally tubular structure may be described by: (Kidney Curl-HIVS)-LIVS (5 mm; each portion of a band of the generally tubular structure is exposed to UV radiation for 20 seconds)-HIVS (4 cm)-LIVS (5 mm; each portion of a band in the generally tubular structure is exposed to UV radiation for 30 seconds)-HIVS (4 cm)-LIVS (5 mm; each portion of a band of the generally tubular structure is exposed to UV radiation for 40 seconds)-(HIVS-Bladder Curl).

As mentioned previously, a medical device of the present disclosure may be, or may include, a generally tubular structure that is hollow. Optionally, such a medical device is or comprises a mesh tube, i.e., a tube formed from a mesh, i.e., the sidewall of the generally tubular structure has a mesh construction, and the interior of the tube is open space. Optionally, the tubular structure is characterized by its length and/or its width, where width refers to the diameter of a cross-section of the generally tubular structure. The generally tubular structure may have a length of at least 5 cm, or at least 6 cm, or at least 7 cm, or at least 8 cm, or at least 9 cm, or at least 10 cm, and not more than 30 cm, or not more than 28 cm, or not more than 26 cm, or not more than 24 cm, or not more than 22 cm, or not more than 20 cm.

In one embodiment, the medical device of the present disclosure comprises a generally tubular structure having a sidewall, wherein the sidewall comprises a monofilament coil encircling the (open) lumen of the generally tubular structure, a mesh that overlays the monofilament coil, and a coating deposited on the coil and the mesh. With this construction, the sidewall comprises three components: the monofilament coil, the mesh, and a coating. This construction may be used to prepare a stent, which is a representative medical device of the present disclosure. When the stent is a urethral stent, the stent may further comprise a kidney-retaining structure at the proximal end of the device and a bladder-retaining structure at the distal end of the device. A kidney-retaining structure is inserted into the kidney of the host and anchors the proximal end of the stent in the kidney. A bladder-retaining structure is inserted into the bladder of a host and anchors the distal end of the stent in the bladder. Optionally, the kidney-retaining structure may be in a form of a curl at the proximal end of the device and a bladder-retaining structure may also be in a form of a curl at the distal end of the device.

When the device contains a coating as part of the generally tubular structure, that coating may or may not have a uniform thickness along the length of the generally tubular structure. In one embodiment, the coating thickness is uniform along the length of the generally tubular structure. In another embodiment, the coating thickness is non-uniform along the length of the generally tubular structure. Non-uniformity in coating thickness can be used to influence the rate of biodegradation of the generally tubular structure. For instance, when a thicker coating is present on the proximal end of the device, biodegradation will preferentially occur at the distal end of the device, all other factors being equal. In one embodiment, the present disclosure provides a ureteral stent having a kidney-retaining structure at the proximal end of the device and a bladder-retaining structure at the distal end of the device, the device comprising a coating on the exterior surface of the device, wherein the proximal end of the device comprises more coating, e.g., a thicker coating, compared to the distal end of the device. This medical device may also have HIVS and LIVS bands as described previously.

In general, medical devices of the present disclosure may be made from biostable or non-biostable materials, where non-biostable materials are referred to herein as degradable materials, and may be known in the art as any of biodegradable, absorbable or bioabsorbable, erodible or bioerodable, soluble or biosoluble. Degradable polymers are capable of being completely eroded or absorbed when exposed to bodily fluids such as blood and can be gradually resorbed, absorbed and/or eliminated by the body. Some degradable materials absorb due to chemical degradation that occurs to the material upon exposure to bodily fluid such as may be found in the vascular environment of a host. Chemical degradation refers to degradation of a material due to chemical reaction of the material with bodily fluids or substances within bodily fluids. The chemical degradation can be the result of hydrolysis, oxidation, enzymolysis, and/or metabolic processes, etc. The chemical degradation can result in, for example, a decrease in molecular weight, deterioration of mechanical properties, and decrease in mass due to erosion. Mechanical properties may correspond to strength and modulus of the material. Deterioration of the mechanical properties of the material decreases the ability of a medical device made therefrom to function optimally in the host. For example, if the device is a stent, the stent provides diminishing mechanical support in a vessel as it degrades. Additionally, some degradable materials are water soluble. A water soluble material refers to a material that is capable of dissolving in water in addition to, or even in the absence of chemical degradation of the material.

In one embodiment, the degradable medical device is formed, in whole or in part from a degradable organic polymer. The organic polymer may be, for example, thermoplastic or thermoset or elastomeric polymer. The organic polymer may be a copolymer, where copolymers are made from two or more different monomers so as to provide properties that are not readily available from a homopolymer. The organic polymer may be in admixture with one or more different polymers, such as one or more different organic polymers. Thus, the various degradable organic monomers as identified herein may be used in concert to prepare a homopolymer or a copolymer, and the various organic polymers as identified herein may be used in combination to prepare an admixture. The medical devices of the present disclosure are at least partially, and optionally completely, degradable, and accordingly will contain some degradable components. In one embodiment, the medical device is made entirely from degradable materials, and thus the medical device is completely degradable. In another embodiment, the medical device is mostly made from degradable materials, and thus at least 50 wt % of the medical device is degradable. In another embodiment, the medical device is made from both degradable and biostable materials, and thus less than 100% of the medical device will degrade. In various embodiments, 100% or up to 95%, or up to 90%, or up to 85%, or up to 80%, or up to 75%, or up to 70%, or up to 65%, or up to 60%, or up to 55%, or up to 50%, or up to 45%, or up to 40%, or up to 35%, or up to 30%, or up to 25% of the medical device is made from degradable material(s), these percentage values being wt % based on the weight of the implantable medical device.

Examples of degradable polymers which may be used to prepare a medical device of the present disclosure include poly(alpha-hydroxy acid) polymers and copolymers, such as polymers and copolymers of glycolide including polyglycolide (PGA), poly(glycolide-co-lactide)(PGLA), and poly(glycolide-co-trimethylene carbonate(PGA/TMC; polymers and copolymers of polylactide (PLA) including poly-L-lactide (PLLA), poly-D-lactide (PDLA), poly-DL-lactide (PDLLA), poly(lactide-co-tetramethylene glycolide), poly(lactide-co-trimethylene carbonate), poly(lactide-co-delta-valerolactone), poly(lactide-co-epsilon-caprolactone), poly(glycine-co-DL-lactide) and poly(lactide-co-ethylene oxide); polydioxanone polymers such as asymmetrically 3,6-substituted poly-1,4-dioxane-2,5-diones; poly(beta-hydroxybutyrate) (PHBA) and copolymers of the same such as poly(beta-hydroxybutyrate-co-beta-hydroxyvalerate); polygluconate; poly(beta-hydroxypropionate) (PHPA); poly(beta-dioxanone)(PDS); poly(delta-valerolactone); poly(ε-caprolactone); methylmethacrylate-N-vinylpyrrolidone copolymers; polyester amides; polyesters of oxalic acid; polydihydropyranes; poly(alkyl-2-cyanoacrylate); polyvinyl alcohol (PVA); polypeptides; poly(beta-maleic acid) (PMLA); poly(beta-alkanoic acid); poly(ethylene oxide) (PEO); polyanhydrides, polyphosphoester, and chitin polymers.

In one embodiment the organic polymer is a polyester, and the generally tubular structure is made largely or entirely from bioabsorbable polyester. For example, the polymer may be a polyester selected from poly(α-hydroxy acid) homopolymers, poly(alpha-hydroxy acid) copolymers and blends thereof. In addition or alternatively, the polyester may be selected from polyglycolide, poly-L-lactide, poly-D-lactide, poly-DL-lactide, and blends thereof. The polyester may be selected from polymers and copolymers of polylactide (PLA), including poly-L-lactide (PLLA), poly-D-lactide (PDLA), poly-DL-lactide (PDLLA).

In one embodiment, the organic polymer is semicrystalline, or is capable of being formed into fibers, or is both semicrystalline and fiber forming. In one embodiment, a medical device is prepared using an organic polymer that is at least one of semicrystalline and fiber-forming. In one embodiment, a degradable stent is prepared with an organic polymer that is both semicrystalline and fiber forming. To additionally make the organic polymer fast-degrading, i.e., having low in vivo stability, glycolide may be used as the, or one of the, monomer(s) used to form the organic polymer. Para-dioxane (PDO) is another suitable monomer for forming fast-degrading (LIVS) organic polymers, where the corresponding homopolymer is known as poly(PDO). Poly (PDO) typically degrades more slowly that glycolide-based polymer, so in order to prepare a very fast degrading organic polymer, the monomer feed is preferably rich in glycolide.

In one embodiment, the organic polymer has a polyaxial structure, while in another embodiment the organic polymer is linear. The polyaxial structure may be a part of the organic polymer, for example, it may be present in a block of a block copolymer. Another option is for the organic polymer to be a segmented polyaxial that is semicrystalline and fiber-forming, and glycolide-based to ensure fast degradation, i.e., low in vivo stability (LIVS). Yet another option is to use linear copolymers for either or both of: diblock, triblock, pentablock, wherein the central block is amorphous and the other blocks are semicrystalline, except for the pentablock, which may be PEG as the central block with amorphous segments connected to the outer crystalline segments (forming a symmetrical pentablock polymer that is a polyether-ester; all other polymers being referred to are aliphatic polyesters). The linear block copolymers may also be comprised of semicrystalline blocks in all cases, with no amorphous blocks, resulting in polymers that can be oriented after fiber formation to create alternating patterns of different crystalline structure and percentage in the fiber, such that there is slight differences in degradation profile of the alternating blocks forming the fiber (as a fiber is oriented, horizontal strips of crystalline regions form and align the blocks comprising the polymer chain). Alternatively, unblocked linear copolymers can be substituted. In one embodiment, these organic polymers are used to form fibers, and the fibers are used to form a coating on the, or as part of the, sidewall of a generally tubular structure which is a component of a medical device of the present disclosure. In another embodiment, these organic polymers are not formed into fibers, however the organic polymer is used to form a coating on the medical device, e.g., by spraying a solution of the polymer onto the medical device, or by dip coating the device into a solution of organic polymer, etc.

The medical device may be made from a base polymer that is amorphous, compliant and elastomeric. It can also be crystallizable, but too much crystallinity typically reduces the compliant nature of the polymer. If a higher crystalline material is chosen for use, then it may be advisable to combine the crystalline material with a plasticizer such as PEG in order to reduce the final crystallinity of the polymer, e.g., the final crystallinity of the coating that is applied to the medical device. As mentioned above, the polymer can be polyaxial or linear, blocked or segmented or random. For a highly flexible and compliant coating, the organic polymer(s) may be minimally crystallinity or may be amorphous.

The organic polymer may be prepared from a prepolymer and end-graft(s) if it is a block copolymer, or it may not be prepared from a prepolymer. In one embodiment, one or more monomers used to prepare the polymer are selected from caprolactone, trimethylene carbonate, and/or l-lactide. Incorporating these monomers into the monomer feed used to prepare the polymer, particularly when glycolide is also used as a monomer, extends the degradation time frame beyond that of a polymer made solely from glycolide.

Suitable degradable organic polymers other than polyesters include polyether-esters, polyether-ester-urethanes (bioabsorbable urethanes), polyether-urethanes and polyether-urethane-ureas, the latter examples being very slowly and typically incompletely degradable.

In various embodiment, the medical device is made from any of the following polymers. MG-5 (Poly-Med, Anderson, SC), which has >65% glycolide in end-graft, is a semicrystalline, polyaxial block copolyester, prepared in a two-step reaction from an amorphous prepolymer and crystalline end graft. MG-9 (Poly-Med, Anderson, SC), which has >80% glycolide, is a semicrystalline, polyaxial block copolyester, prepared in a two-step reaction from an amorphous prepolymer and crystalline end graft. A semicrystalline, polyaxial segmented copolyester prepared in a single step reaction (no prepolymer is used). A semicrystalline, linear block copolyester, prepared in a two-step reaction from an amorphous prepolymer and crystalline end graft. A triblock copolymer with crystalline end grafts. A diblock copolymer. A semicrystalline, linear segmented copolyester prepared in a single step reaction (i.e., no prepolymer is used). SVG-12 (Poly-Med, Anderson, SC) having an inherent viscosity of greater than 1.0, having a crystallizable end graft. A polyaxial block copolymer. A polymer prepared from an amorphous prepolymer and amorphous end graft. A linear block copolymer (triblock, diblock, pentablock). A linear, segmented copolymer. A linear random copolymer which is amorphous and thus is both compliant and flexible. The foregoing are exemplary only of the organic polymers that may be used to prepare a suitable medical device, or component thereof such as a coating layer.

Another suitable polymer for preparing a medical device of the present disclosure is a mixture comprising (a) a bioerodible polyester network formed by reaction between reactive species that comprise a polyol and a polycarboxylate, wherein at least one of the polyol and polycarboxylate has a functionality of three or more, and (b) a bioerodible thermoplastic polymer. Optionally, one or more of the following may further characterize this compositions: the polyol is selected from a non-polymeric diol, a polymeric diol, a non-polymeric triol, a polymeric triol; the polycarboxylate is selected from a non-polymeric dicarboxylate, a polymeric dicarboxylate, a non-polymeric tricarboxylate, and a polymeric tricarboxylate; the reactive species comprise a triol, a tricarboxylate, or both; the reactive species comprise (a) non-polymeric tricarboxylate and (b) a polyester polyol; the reactive species comprise (a) citric acid and (b) a polycaprolactone diol, a polycaprolactone triol or both; the bioerodible thermoplastic polymer has a melting point above body temperature; the bioerodible thermoplastic polymer has a glass transition temperature below room temperature; and the bioerodible thermoplastic polymer is a bioerodible thermoplastic polyester. See, e.g., U.S. Patent Publication No. 20160166739.

In one aspect, the implantable medical devices of the present disclosure include a coating as a component of the medical device. The location of the coating relative to the medical device, and the properties of the coating in terms of physical and chemical properties, both assist in managing the degradation and/or elimination of the medical implant from the host. In particular, the coating serves, in part, to manage the degradation and/or elimination of the medical device from the host. The properties of the coating may be selected with a view to managing the degradation and/or elimination of the coated medical device from the host.

The medical devices present in the medical implants of the present disclosure are degradable to at least some extent. In other words, the medical device will degrade when placed into the host. That degradation may be a physical or chemical degradation. Physical degradation refers to a change in the physical or mechanical properties of the medical device. For example, the device may break down into pieces, and thus lose its integrity. As another example, the device may soften and become compliant. As yet another example, the device may absorb fluid and swell. In each of these cases, the device undergoes a change in physical or mechanical properties. Chemical degradation refers to a change in chemical composition. For example, an organic polymer from which the device is made may undergo hydrolytic bond cleavage or enzymatically-induced bond cleavage, and thereby lose molecular weight. As another example, water-soluble components of the medical device may dissolve in water and leave the vicinity of the medical device. In each of these example, the chemical degradation produces a change in the chemical description of the medical device. In one embodiment, degradation of the medical implant occurs by both of physical and chemical degradation. The coating of the medical implant may serve, in part or entirely, to influence this degradation. Thus, the properties of coating may be used to manage the degradation and/or elimination of the medical implant from the host.

In one aspect, the medical device includes a coating on a portion of the medical device, where the coating functions as containment layer. This containment layer provides a physical barrier between the tissue of a host and the medical device. Such a barrier is useful, for example, when the device degrades by breaking into pieces and it is desired to manage the dispersement or dissemination of those pieces. For example, in one embodiment the containment layer may be relatively long-lasting compared to the medical device, so that as the medical devices is breaking into pieces, the containment layer is maintaining sufficient structural integrity that those pieces are retained within the containment layer. Such a containment layer is useful when the medical device is placed in the kidney and it is undesirable that pieces from the medical device should contact the inside of the kidney and calcify. In a related embodiment, the containment layer is again relatively long lasting compared to the medical device which is an esophageal stent. In this case, if the esophageal stent breaks into pieces, the containment layer which is located in and surrounds the lumen wall of the stent, will deter those pieces from passing into the stomach. Thus, in either example the containment layer effectively restricts the movement pieces of the medical device.

In another aspect, the medical device does not have a containment layer. In this situation, the medical device does not have a feature, e.g., a containment layer, which restricts the movement of the fragments, e.g., HIVS bands, which form upon degradation of the medical device, e.g., by degradation of LIVS bands adjacent to the HIVS bands. Optionally, the generally tubular structure, which is a portion of the medical device, does not include a containment layer that restricts the movement of fragments such as HIVS bands formed upon degradation of the generally tubular structure. In the absence of a containment layer or equivalent feature, the fragments that form during in vivo degradation of a medical device or generally tubular structure of the present disclosure, are free to disassociate from the medical device and leave the vicinity of the implanted medical device. In each of the embodiments disclosed herein, it may be mentioned that the medical device or any portion thereof does not have a containment layer.

In another aspect, the containment layer provides a physical or chemical barrier between the degradation-inducing fluids of the host and the medical device. This layer can be used to influence the spatial and temporal degradation of the medical device. For example, in one embodiment the containment layer is a discontinuous layer such that the layer covers some but not all of the medical device. In this situation, the containment layer effectively acts as a barrier between a portion of the medical device and the degradation-causing fluid of the host, which restricts contact between a portion of the medical device and the fluid. The containment layer thereby allows the exposed portion(s) of the medical device to degrade more quickly than will the nonexposed portion(s) of the medical device. In this way, the containment layer is used to manage where the device will initially degrade.

In another embodiment, a graduated containment layer is used to manage the spatial and temporal degradation and/or elimination of the medical device. For example, a medical device may have a single coating layer over a first portion of the device, a double coating layer over a second portion of the device, and optionally a triple coating layer over a third portion of the device. Assuming the composition of the coating layer is the same at each location, the first portion of the medical device will degrade before the second and third portions of the device. Depending on the relative thicknesses at each location, the first portion may significantly degrade and be eliminated from the host, while the second and third portions of the device are still significantly intact. Depending on how the layers are arranged, the degradation and elimination of the first portion of the medical device may allow increased access of biological fluid to the second portion of the medical device, with the result that the second portion will undergo degradation even though the second portion may still be covered by the coating. The second portion of the device will undergo degradation and elimination, followed by degradation and elimination of the third portion of the device. In this example, the coating manages the rate at which various portions of a medical device degrade and are eliminated from the host. However, it should be noted that the coating may also function as a containment layer to manage the dispersement or dissemination of those pieces, i.e., to restrict the movement of those pieces within the host.

The medical implant, including one or both of the medical device itself and coating(s) thereon, may include a therapeutic agent. The amount of the therapeutic agent incorporated into the implant will depend on the nature of the implant, the actual therapeutic agent, the condition of the subject, and so forth. The amount may be readily determined by those of ordinary skill in the art. Exemplary therapeutic agents include anti-thrombotic agents, anti-proliferative agents, anti-inflammatory agents, anti-migratory agents, antineoplastic agents, anti-mitotic agents, anesthetic agents, and anti-coagulants. Addition suitable therapeutic agents include agents that affect extracellular matrix production and organization, vascular cell growth (either promoters or inhibitors), cholesterol-lowering agents, vasodilating agents, and agents that interfere with endogenous vasoactive mechanisms.

In various embodiments of the present invention, the medical device may be an ureteral stent. The medical device, e.g., the ureteral stent, may be designed to release one or more drugs where representative examples of drugs include one or more suitable members of the following: alpha-adrenergic blockers, analgesic agents, anti-cancer agents, antineoplastic agents, anti-inflammatory agents, anti-microbial agents, antiproliferative agents, anti-spasmodic agents, beta-adrenergic agonists, bronchodilators (e.g., for muscle relaxant properties), calcium channel blockers, corticosteroids, anesthetic agents, narcotic analgesic agents, nitric oxide donors, nitric oxide releasing compounds, non-narcotic analgesic agents, prostaglandins, and among others, as well as combinations thereof.

Additional representative examples of drugs include one or more of the following: Angiogenesis Inhibitors, 5-Lipoxygenase Inhibitors and Antagonists, Chemokine Receptor Antagonists CCR (1, 3, and 5), Cell Cycle Inhibitors, Cyclin Dependent Protein Kinase Inhibitors, EGF (Epidermal Growth Factor) Receptor Kinase Inhibitors, Elastase Inhibitors, Factor Xa Inhibitors, Farnesyltransferase Inhibitors, Fibrinogen Antagonists, Guanylate Cyclase Stimulants, Heat Shock Protein 90 Antagonists, HMGCoA Reductase Inhibitors, Hydroorotate Dehydrogenase Inhibitors, IKK2 Inhibitors, IL-1, ICE and IRAK Antagonists, IL-4 Agonists, Immunomodulatory Agents, Inosine monophosphate dehydrogenase inhibitors, Leukotriene Inhibitors, MCP-1 Antagonists, MMP Inhibitors, NF kappa B Inhibitorsm NO Agonists, P38 MAP Kinase Inhibitors, Phosphodiesterase Inhibitors, TGF beta Inhibitors, TNFa Antagonists and TACE Inhibitors, Tyrosine Kinase Inhibitors, Vitronectin Inhibitors, Fibroblast Growth Factor Inhibitors, Protein Kinase Inhibitors, PDGF Receptor Kinase Inhibitors, Endothelial Growth Factor Receptor Kinase Inhibitors, Retinoic Acid Receptor Antagonists, Platelet Derived Growth Factor Receptor Kinase Inhibitors, Fibronogin Antagonists, Antimycotic Agents, Bisphosphonates, Phospholipase A1 Inhibitors, Histamine H1/H2/H3 Receptor Antagonists, Macrolide Antibiotics, GPIIb IIIa Receptor Antagonists, Endothelin Receptor Antagonists, Peroxisome Proliferator-Activated Receptor Agonists, Estrogen Receptor Agents, Somatostatin Analogues, Neurokinin 1 Antagonists, Neurokinin 3 Antagonist, Neurokinin Antagonist, VLA-4 Antagonist, Osteoclast Inhibitor, DNA topoisomerase ATP Hydrolysing Inhibitor, Angiotensin I Converting Enzyme Inhibitor, Angiotensin II Antagonist, Enkephalinase Inhibitor, Peroxisome Proliferator-Activated Receptor Gamma Agonist Insulin Sensitizer, Protein Kinase C Inhibitor, CXCR3 Inhibitors, Itk Inhibitors, Cytosolic phospholipase A2-alpha Inhibitors, PPAR Agonist, Immunosuppressants, Erb Inhibitor, Apoptosis Agonist, Lipocortin Agonist, VCAM-1 antagonist, Collagen Antagonist, Alpha 2 Integrin Antagonist, TNF Alpha Inhibitor, Nitric Oxide Inhibitor, and Cathepsin Inhibitor.

Examples of alpha-adrenergic blockers include: alfuzosin, amosulalol, arotinilol, dapiprazole, doxazosin, ergoloid, fenspiride, idazoxan, indoramin, labetalol, manotepil, mesylates, naftopidil, nicergoline, prazosin, tamsulosin, terazosin, tolazoline, trimazosin, and yohimbine.

Examples of anesthetic agents include: benzocaine, cocaine, lidocaine, mepivacaine, and novacaine.

Examples of beta-adrenergic agonists include: albuterol, bambuterol, bitolterol, carbuterol, clenbuterol, clorprenaline, denopamine, ephedrine, epinephrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, prenalterol, procaterol, protokylol, reproterol, rimiterol, ritodrine, salmerterol, soterenol, terbutaline, tretoquinol, tulobuterol and xamoterol.

Examples of anti-cancer, anti-proliferative and antineoplastic agents include: agents affecting microtubule dynamics (e.g., colchicine, Epo D, epothilone, paclitaxel, vinblastine, vincristine, etc.), alkyl sulfonates, angiogenesis inhibitors (e.g., angiostatin, endostatin, squalamine, etc.), antimetabolites such as purine analogs (e.g., 6-mercaptopurine or cladribine, which is a chlorinated purine nucleoside analog, etc.), pyrimidine analogs (e.g., 5-fluorouracil, cytarabine, etc.) and antibiotics (e.g., daunorubicin, doxorubicin, etc.), caspase activators, cerivastatin, cisplatin, ethylenimines, flavopiridol, limus family drugs (e.g., everolimus, sirolimus, tacrolimus, zotarolimus, etc.), methotrexate, nitrogen mustards, nitrosoureas, proteasome inhibitors, and suramin.

Examples of antimicrobial agents include: benzalkonium chlorides, chlorhexidine, nitrofurazone, silver particles, silver salts, metallic silver and antibiotics, such as gentamicin, minocycline and rifampin, triclosan.

Examples of bronchodilators include: (a) ephedrine derivatives such as albuterol, bambuterol, bitolterol, carbuterol, clenbuterol, clorprenaline, dioxethedrine, ephedrine, epinephrine, eprozinol, etafedrine, ethylnorepinephrine, fenoterol, formoterol, hexoprenaline, isoetharine, isoproterenol, mabuterol, metaproterenol, n-methylephedrine, pirbuterol, procaterol, protokylol, reproterol, rimiterol, salmeterol, soterenol, terbutaline and tulobuterol, (b) quaternary ammonium compounds such as bevonium methyl sulfate, flutropium bromide, ipratropium bromide, oxitropium bromide and tiotropium bromide, (c) xanthine derivatives such as acefylline, acefylline piperazine, ambuphylline, aminophylline, bamifylline, choline theophyllinate, doxofylline, dyphylline, etamiphyllin, etofylline, guaithylline, proxyphylline, theobromine, 1-theobromineacetic acid and theophylline, and (d) other bronchodilators such as fenspiride, medibazine, methoxyphenanime and tretoquinol, among others, as well as combinations and pharmaceutically acceptable salts, esters and other derivatives of the forgoing.

Examples of calcium channel blockers include: arylalkylamines (including phenylalkylamines) such as bepridil, clentiazen, fendiline, gallopamil, mibefradil, prenylamine, semotiadil, terodiline and verapamil, benzothiazepines such as diltiazem; calcium channel blockers such as bencyclane, etafenone, fantofarone, monatepil and perhexiline, among other calcium channel blockers; dihydropyridine derivatives (including 1,4-dihydropyridine derivatives) such as amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine and nitrendipine, piperazine derivatives such as cinnarizine, dotarizine, flunarizine, lidoflazine and lomerizine.

Examples of corticosteroids include: betamethasone, cortisone, deflazacort, dexamethasone, hydrocortisone, methylprednisolone, prednisolone, prednisone and triamcinolone, among others, as well as combinations and pharmaceutically acceptable salts, esters and other derivatives of the same.

Examples of nitric oxide donors/releasing molecules include: inorganic nitrates/nitrites such as amyl nitrite, isosorbide dinitrate and nitroglycerin, inorganic nitroso compounds such as sodium nitroprusside, sydnonimines such as linsidomine and molsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of, natural polymers/oligomers, oligosaccharides, peptides, polysaccharides, proteins, and synthetic polymers/oligomers), as well as C-nitroso-compounds, L-arginine, N-nitroso-compounds, and O-nitroso-compounds.

Examples of prostaglandins and analogs thereof for use in the present disclosure may be selected from suitable members of the following: prostaglandins such as PGE1 and PGI2 and prostacyclin analogs such as beraprost, carbacyclin, ciprostene, epoprostenol, and iloprost.

Examples of narcotic analgesic agents include: codeine, fentanyl, hydromorphonein, levorphanol, meperidine, methadone, morphine, oxycodone, oxymorphone, propoxyphene, and pentazocine, among others, as well as combinations and pharmaceutically acceptable salts, esters and other derivatives of the same.

Examples of non-narcotic analgesic agents include: analgesic agents such as acetaminophen, and non-steroidal anti-inflammatory drugs such as aspirin, celecoxib, diflunisal, diclofenac, etodolac, fenoprofen, flurbiprofen, ibuprofen, ketoprofen, ketorolac, meclofenamate, meloxicam, nabumetone, naproxen, naproxen indomethacin, oxaprozin, piroxicam, salsalate, sulindac, tolmetin, and valdecoxib.

The medical device of the present disclosure, e.g., a ureteral stent, may be manufactured to contain and release one or more of these or other therapeutic agents. In addition to the drugs listed herein, pharmaceutically acceptable salts, esters, and other derivatives of the drugs can also be utilized. The drugs provided herein can be loaded, for example, into a polymeric component of the medical device. When the medical device is a stent, the drug may be incorporated into the coil, a knitted construct that adjoins the coil, or a coating which impregnates the knitted construct.

Urologically beneficial drugs may be may be associated with the drug releasing stent in various ways, including the following, among others: (a) loaded in the interior (bulk) of a stent component, e.g., the monofilament coil, or a multifilament knitted construct, or a coating or sleeve or sheath, (b) bound to a surface of the stent, such as a surface of the monofilament coil, or the surface of the multifilament knitted construct, or a coating or a sleeve or sheath that forms a part of the stent, where the drug is bound to the surface by any of covalent interactions and/or non-covalent interactions (e.g., interactions such as van der Waals forces, hydrophobic interactions and/or electrostatic interactions, for instance, charge-charge interactions, charge-dipole interactions, and dipole-dipole interactions, including hydrogen bonding), (c) applied as a coating that covers all or a portion of the stent or a component thereof, (d) loaded in surface features (e.g., depressions) of the stent or a component thereof, and (e) combinations of the forgoing.

The amount of urologically beneficial drug(s) associated with the drug-releasing stent should be a therapeutically or prophylactically effective amount, where that amount may range, for example, from than 1 wt % or less to 2 wt % to 5 wt % to 10 wt % to 25 wt % to 50 wt % or more, depending the particular drug and the desired effect.

In one embodiment of a medical device including a drug, the present disclosure provides a medical device for placement in a body of a mammal, comprising: a polymeric matrix forming the device and defining a lumen through the device, the matrix comprising polymer macromolecules and defining spaces between the polymer macromolecules; a drug contained within at least some of the spaces of the matrix; and a material contained within at least some of the spaces of the matrix to affect diffusion of the drug out of the polymeric matrix when the medical device is placed in the body of the mammal. Optionally, one or more of the following may further characterize a medical device of the present disclosure: each of the polymeric material and the drug has a molecular weight where the molecular weight of the drug is less than the molecular weight of the polymeric material; the quantity of drug associated with the device is between 0.1 and 50 weight percent of the weight of the device; the medical device is a ureteral stent or a catheter; the polymeric component comprises a degradable polyester; the polymeric component is hydrophobic; at least some of the spaces that contain the drug also contain polymeric material; the drug comprises oxybutynin chloride or ketorolac; the material in association with the drug comprises polyethylene glycol (PEG); the drug is in association with a biodegradable material; the drug is in association with a material from which the drug must dissociate before diffusing out of the polymeric matrix; the polymeric matrix is coated onto the device.

Thus, the medical device can be used as a vehicle to deliver one or more drugs to the body of a patient. A ureteral stent, catheter, and/or other medical device can be used to deliver the drug(s) by placing the device entirely or partially in the body of a patient. By using certain material(s) and drug(s) in a polymeric matrix, the diffusion of the drug(s) out of the matrix can be controlled in ways previously unachievable. One or more drugs may thereby be administered to the patient's body over a sustained time (ranging from days to months, for example) and at a relatively constant, and therapeutic, level.

A drug-delivering medical device according to the present disclosure may be formed entirely or partially of a polymeric matrix, loaded with the drug(s) and material(s) that affect the diffusion of the drug(s) out of the matrix when the device is placed in the body of a human or other mammal. The device can be a ureteral stent, a catheter, a dialysis tube, a cannula, a urethral stent, a suture, or other medical device designed for placement (entirely or partially) in the body. A device according to the present disclosure may optionally be coated entirely or partially with such a loaded polymeric matrix. For example, a hydrophobic polymeric matrix can coat all or some portion of a lead wire, a stent, or a catheter.

In another embodiment, the present disclosure provides a ureteral stent comprising an elongated stent body, a deployable retention structure, and a drug-releasing member selected from (i) a sleeve of drug-releasing material that is disposed over at least a portion of the deployable retention structure, (ii) a sheet of drug-releasing material that is attached to the deployable retention structure and (iii) a sheet of drug-releasing material connected to a sleeve of material that is disposed over at least a portion of the deployable retention structure. Optionally, one or more of the following features may further describe this drug-releasing ureteral stent: a sleeve of drug-releasing material is disposed over at least a portion of the deployable retention structure, where optionally the sleeve is a biodisintegrable sleeve and/or the sleeve is a heat shrinkable sleeve and/or the sleeve ranges from 1 to 4 mm in inner diameter, from 2 to 500 mm in length and from 50 to 200 micrometers in thickness; the stent comprises a sheet of drug-releasing material that is attached to the deployable retention structure, where optionally, the sheet is a biodisintegrable sheet and/or the sheet is an elastic sheet and/or the sheet ranges from 2 to 20 mm in width, from 2 to 500 mm in length and from 50 to 200 micrometers in thickness; the stent includes a retention structure in the form of a coil or a loop and wherein the sheet of drug-releasing material spans a majority of the coil or loop area upon deployment of the retention structure; the stent includes a sheet of drug-releasing material connected to a sleeve of material that is disposed over at least a portion of the deployable retention structure; the stent includes a retention structure which is a kidney retention structure configured to be delivered through the ureter and deployed in the kidney, where optionally the retention structure is adapted to be reduced to a profile that is sufficiently small during deployment to allow the retention structure to be delivered to the kidney; the stent has a retention structure that comprises a plurality of elongated elements to which the sheet of drug-releasing material is attached and between which the sheet of drug-releasing material is situated upon deployment of the retention structure; the stent body and deployable retention structure comprise a biostable polymer.

Loading of the drug into the polymer may be between about 0 to 20 weight percent of the device depending on the nature of the material, the quantity of the polymer, the release profile of the polymer, the release profile of the drug, the desired drug diffusion effect, and the desired period for drug delivery, among other factors. In one embodiment, loading of the drug is between about 1 to 10 weight percent of the device.

Materials may be added to the polymer composition specifically to influence the release of the drug from the polymer. Such materials include, without limitation, styrenethylene-butylene-styrene (SIBS), collagen, alginates, carboxymethyl cellulose (CMC), hydroxypropyl cellulose (HPC), dextrin, plasticizers, lipophilic material and other fatty acid salts, pore formers, sugar, glucose, starch, hyaluronic acid (HA), chelating agents, including ethylenediaminetetraacetic acid (EDTA), polyethylene glycol (PEG), polyethylene oxide (PEO), and copolymers thereof. Multiple materials of varying release profiles may be incorporated within the polymeric composition with the drug(s) to achieve the desired drug release profile.

In one aspect, the present disclosure provides a bioabsorbable medical implant that is partially covered by an outer containment layer, where the containment layer is either nonbioabsorbable, or is at least partially bioabsorbable but does not degrade as quickly as does the medical implant. In one embodiment, in vivo, the medical implant will degrade into pieces while the outer layer retains sufficient structural integrity to provide a barrier which cannot be crossed by the pieces from the implant. In this way, the pieces are constrained to staying in a localized area where they cannot cause any harm to the host. In fact, even as the pieces degrade, the resulting smaller pieces and ultimately the molecular components of the implant, will all stay within the outer containment layer, and together may be conducted to a place that is safe for elimination.

GRADIENTS

In one aspect, the medical device is characterized as having a gradient. A gradient refers to variation in some property, e.g., composition, of the medical device as a function of a direction. This gradient provides for variation in degradation along the gradient. For example, the average molecular weight of the polymer that forms the medical device may vary along a direction of the medical device, such that the polymer at the distal end of the medical device or a portion thereof has a higher average molecular weight than does the polymer at a proximal end of the medical device or a portion thereof. In this way, the proximal end of the medical device or portion thereof may degrade more rapidly than does the distal end where the polymer has a higher initial average molecular weight. The provision of a gradient in the medical devices of the present disclosure provides a mechanism for managed degradation of the device. In one embodiment, the gradient does not impact or effect the functionality of the medical device, but only impacts the degradation profile of the device. Such nonhomogeneity in the medical device may be referred to herein as the gradient of the medical device, and a medical device having such a gradient may be referred to as a graduated medical device.

Optionally, a coating or containment layer of the present disclosure may be characterized in terms of having a gradient, such that the coating or containment layer that covers one portion of a medical device is different from the coating or containment layer that covers another portion of the medical device. Such nonhomogeneity in the coating or containment layer will be referred to herein as the gradient in the coating or containment layer, and the coating having such a gradient may be referred to herein as a graduated coating, while a containment layer having such a gradient may be referred to as a graduated containment layer.

Gradients may be formed in various ways. For example, different compositions, having different degradation rates, may be used to form the different portions of the medical device. Thus, a composition having a relatively high degradation rate may be used to form a first portion of a medical device while a composition having a relatively slower degradation rate may be used to form a second portion of the medical device. In this way, the device will degrade more quickly in some places than in other places.

As another example, a single composition may be used to form a graduated coating or containment layer. For instance, a single composition may be coated to a first thickness over a first portion of a medical device while the same composition is used to create a coating having a second thickness over a second portion of the medical device. In general, a thicker coating will be retained for a longer time on the medical device than will a thinner coating, or in other words, a thicker coating will degrade more slowly than a thinner coating, all other factors being equal. A thicker coating may be formed, for example, by repeatedly coating a region of the containment layer where greater coating thickness is desired.

The thickness of the coating or containment layer may vary throughout the medical implant. However, at its thickest point, in various embodiments, the coating or containment layer has a thickness of greater than 10 microns, or greater than 20 microns, or greater than 30 microns, or greater than 40 microns, or greater than 50 microns, or greater than 60 microns, or greater than 70 microns, or greater than 80 microns, or greater than 90 microns, or greater than 100 microns, or greater than 110 microns, or greater than 120 microns, or greater than 130 microns, or greater than 140 microns, or greater than 150 microns, or greater than 160 microns, or greater than 170 microns, or greater than 180 microns, or greater than 190 microns, or greater than 200 microns. The maximum thickness may be 500 microns, or 400 microns, or 300 microns, or 200 microns, or 150 microns, or 100 microns.

The amount of the coating or containment layer may vary throughout the medical implant. In one aspect, in addition to or instead of specifying a thickness for a coating or containment layer, the coating or containment layer may be characterized in terms of how much organic polymer is present over a given volume of medical device. For example, the amount may be specified in terms of mg organic polymer per square centimeter ($cm^2$) of medical device. In various embodiments, the medical device is covered with a coating or containment layer in the amount of at least 10 $mg/cm^2$; or at least 15 $mg/cm^2$; or at least 20 $mg/cm^2$; or at least 25 $mg/cm^2$; or at least 30 $mg/cm^2$; or at least 35 $mg/cm^2$; or at least 40 $mg/cm^2$; or at least 45 $mg/cm^2$; or at least 50 $mg/cm^2$.

Thus, in one embodiment the present disclosure provides a medical implant comprising a medical device and a graduated coating or graduated containment layer that covers a portion of the medical device. Optionally, the graduated coating or containment layer may comprise multiple thicknesses, e.g., 2, 3, 4, 5, or more than 5 different thicknesses at different locations. The graduated coating or containment layer having multiple thicknesses at different locations may be formed by having various numbers of coating layers of a polymer composition at different locations, and thus may be said to comprise multiple layers of coating composition. Also optionally, the graduated coating or containment layer may comprise multiple compositions, e.g., 2, 3, 4, 5, or more than 5 different compositions at different locations. Optionally, the graduated coating or containment layer may comprise variation in two or more properties, e.g., multiple thicknesses and multiple compositions.

While thickness and composition are examples of variation that may be present in a coating or containment layer, these are exemplary only. Other variations can also be used to create a graduated coating or containment layer according to the present disclosure, for example, variation in texture, variation in hydrophilicity, variation in thermal stability, variation in tensile strength, and variation in fiber density when the coating or containment layer contains fibers, to name a few.

In one embodiment, the containment layer is made from one or more organic polymers. The containment layer may be completely non-biodegradable. However, in another embodiment, the containment layer is biodegradable, but it degrades at a slower rate than the medical device. In this way, if the medical device is degrading into pieces, the containment layer retains its structural integrity and holds the pieces together within a confined space, for a time sufficient for the pieces to degrade into even smaller pieces that are not harmful to the host, and/or into the polymeric and/or monomeric components of the medical device.

In one embodiment, the containment layer is a coating on the medical device. The coating may be present on a position retaining end of the medical device. The coating may be completely non-biodegradable. However, in another embodiment, the coating is biodegradable, but it degrades at a slower rate than the medical device. In this way, if the medical device is degrading into pieces, the coating retains its structural integrity and holds the pieces of the position retaining end together within a confined space, for a time sufficient for the pieces to degrade into even smaller pieces that are not harmful to the host, and/or into the polymeric and/or monomeric components of the medical device.

When a polymer solution is used to form the coating on the medical device, the concentration of polymer in the solution is a factor that must be considered. A higher concentration of polymer will tend to deposit more polymer on the surface of the medical device, when that device is dipped, drawn, or otherwise coated with the polymer so as to form a coating or containment layer.

The containment layer is placed on those portions of the medical device where it is desired to protect the host from damage or injury or trauma due to pieces of the device being formed during biodegradation. For example, in the case of a stent which is implanted into a host, where the stent is placed partially within the host's kidney and partially outside of the kidney, it will be desirable that pieces of disintegrating stent not disperse in kidney and give rise to kidney stones. Accordingly, the portion of the stent that will be placed within the kidney may be coated to provide a containment layer, while the portion of the stent that is placed outside of the kidney, e.g., the generally tubular structure that forms the main central tube of the stent, may not have a containment layer. In this way, a containment layer is present on only a portion of the medical device.

The present disclosure provides that any medical device that degrades by a disintegration process, i.e., by a process whereby the device breaks down into pieces, may be provided with a containment layer. An exemplary device of this type is an endoureteral stent, also called a ureteral stent. The stent is biodegradable and disintegratable so that it initially maintains optimum ureteral patency for a predetermined period of time. However, at the conclusion of this period, the stent will begin to disintegrate into small pieces. In order to preclude those small pieces from traveling, particularly when those small pieces form part of a position retaining end of the stent, the position retaining end(s) of the stent is at least partially encased by a containment layer. The layer retains sufficient integrity such that, during the period of time during which the small pieces are formed and then either degrade into non-harmful pieces, or degrade into their polymeric or molecular components, the containment layer will contain those small pieces. The containment layer thus acts to protect the host from the small pieces that are formed upon disintegration of the stent. The containment layer also protects the host from contact with rigid pieces which are not easily passed out of the body.

In one embodiment, the present disclosure provides ureteral stents which have a diversity of properties at different locations of the stent, but the stent and components thereof are not assembled from multiple segments. Rather, the stent is assembled from a single uniform construct, and that construct is then modified to provide a diversity of properties at different locations of the construct. The diversity may be in one or more properties including biodegradability, radiopacity, stiffness or flexibility, and loading with therapeutic agents. The diversity is created by methods as disclosed herein, e.g., by selectively degrading the stent or a component thereof before it is implant into the host, and other methods disclosed herein. In this way, bands having either higher in vivo stability (HIVS) or bands having lower in vivo stability (LIVS) relative to the unmodified portion of the medical device, may be created. In one embodiment, bands of unmodified material are treated in order to induce them to have lower in vivo stability (LIVS) relative to the adjacent unmodified bands and thereby create LIVS bands. In another embodiment, bands of unmodified material are treated to induce them to have high in vivo stability (HIVS) relative to the adjacent unmodified bands, and thereby create HIVS bands.

In one embodiment, the medical device is a stent, and the stent is a construct of a fiber-reinforced elastomeric film designed with at least one position-retaining end, wherein the fiber-reinforcement is (a) a combination of a monofilament coil and weft-knitted tube multifilament yarn; (b) a combination of monofilament coil and a braided multifilament yarn; (c) a tube comprising a braided or weft-knitted monofilament yarn; or (d) a weft-knitted or braided monofilament yarn in the form of a tube.

In still another embodiment, the stent is a construct of a fiber-reinforced elastomeric film designed with at least one position-retaining end wherein the fiber reinforcement is a combination of a monofilament and knitted or braided multifilament yarn, wherein the fiber reinforced elastomeric film is in the form of a tube with a central, main component having a smaller diameter than that of the patient ureter wherein each of the position-retaining ends defines two freely laterally deformable components formed of initially partially overlapping bitubular ends of the main, central component and a laterally fused tube which are radially and axially cut to produce two over-extended flaps attached to an intact semi-cylindrical extension of the main, central tube.

In yet still another embodiment, the stent is a construct of a fiber-reinforced elastomeric film designed with at least one position-retaining end, wherein the fiber-reinforcement is a monofilament yarn or a combination with knitted or braided multifilament yarn, wherein the fiber-reinforced elastomeric film is in the form of a tube with a smaller diameter than that of the patient ureter and having at least one position-retaining end, wherein the position-retaining end is an angled portion of the main tube having a length comparable to the patient ureter and comprising a flexible hinge that maintains an angle of more than 30 degrees with respect to the main tube in an absence of deforming stress.

In another embodiment, the stent comprises a retention portion configured to help retain the stent in place within a body of a patient; and an elongate portion extending from the retention portion, the elongate portion having a sidewall defining a lumen, the sidewall having a first section and second section, the first section of the sidewall having a first thickness, the second section of the sidewall having a second thickness different than the first thickness. Optionally, the stent may be further characterized by one or more of the following: the retention portion is configured to be disposed within a kidney of the patient; the retention portion is a first retention potion and the stent further comprises a second retention portion configured to help retain the stent in place within the body of the patient; the first section of the sidewall forms an annular ring; the first section of the sidewall forms a spiral; the first section of the sidewall forms a dimple; the sidewall has a third portion, the second portion of the sidewall being disposed between the first portion of the sidewall and the third portion of the sidewall; the sidewall has a third portion, the third portion has a thickness different than the second thickness, the second portion of the sidewall being disposed between the first portion of the sidewall and the third portion of the sidewall; the sidewall has a third portion, the second portion of the sidewall being disposed between the first portion of the sidewall and the third portion of the sidewall, the third portion having a third thickness, the second thickness being greater than the first thickness, the second thickness being greater than the third thickness; the first portion of the sidewall has a first section and a second section, the first section of the first portion forming a spiral rotating in a first direction, the second section of the first portion forming a spiral rotating in a second direction different than the first direction. This stent, including optional embodiments thereof, may be modified by techniques disclosed herein to display managed degradation when the stent is located within a host. For instance, a slit may be made in the slit to provide a site that promotes degradation.

In another embodiment the stent comprises a retention portion configured to help retain the stent in place within a body of a patient; and an elongate portion extending from the retention portion, the elongate portion having a first member and a second member, the first member being devoid of a lumen, the second member being devoid of a lumen, the first member and the second member being intertwined. In another embodiment, the stent comprises a retention portion configured to help retain the stent in place within a body of a patient; and an elongate portion extending from the retention portion and having an expanded configuration and a nominal configuration, the elongate portion having a sidewall defining a lumen extending from a first end portion of the elongate portion to a second end portion of the elongate portion, the sidewall defining a chamber, the chamber being configured to receive a fluid to place the elongate portion in its expanded configuration. Again, either of these stents may be modified by techniques disclosed herein to demonstrate managed degradation with situated within a host.

In another embodiment, the stent is a construct of a fiber-reinforced elastomeric film designed with at least one position-retaining end wherein the fiber reinforcement is a combination of a monofilament and knitted or braided multifilament yarn, wherein the fiber-reinforced film is tubular with a central main component having a smaller diameter than that of the patient ureter and comprising at least one position-retaining end wherein the position-retaining end is a highly flexible extension of the central main tube, acquiring a goose-neck shape after insertion in the patient ureter but can be made co-linear with the central main tube during insertion with an applicator.

In another embodiment, the stent comprises an elongate member having a first portion and a second portion, the second portion having a sidewall that defines a single lumen, the first portion being coupled to the second portion, the first portion configured to be disposed within a kidney of a patient, the sidewall of the second portion of the elongate member is configured to deliver fluid from a first location of the sidewall of the second portion to a second location of the sidewall of the second portion via at least one of capillary action and wicking, the second portion of the elongate member configured to be disposed within at least one of a bladder of a patient and a ureter of the patient, at least a portion of the first portion being disposed within the lumen. Optionally, one or more of the following features may further characterize this stent: the second portion of the elongate member is constructed of a multi-stranded material; the second portion of the elongate member is constructed of a yarn; the second portion of the elongate member has a configuration selected from a group consisting of a braided tube configuration and a long woven strip configuration; the second portion of the elongate member is constructed of a melt spun polypropylene with a high loading of barium sulphate; the stent further comprises a proximal retention structure configured to be disposed within the bladder of a patient, the proximal retention structure being coupled to the second portion of the elongate member; the stent further comprises a distal retention structure configured to be disposed within the kidney of the patent, the distal retention structure being coupled to the first portion of the elongate member; the first portion is coupled to the second portion via an interference fit; the second portion of the elongate member has a substantially solid tubular shape; the second portion of the elongate member is substantially flexible; the first portion of the elongate member is substantially rigid; the second portion of the elongate member is more flexible than the first portion of the elongate member. This stent, including optional embodiments thereof, may be modified to demonstrate managed degradation according to the present disclosure.

In another embodiment, the medical device is a ureteral stent comprising: an elongate member having a first portion and a second portion, the second portion having a substantially solid cylindrical shape, the first portion being coupled to the second portion, the first portion configured to be disposed within a kidney of a patient, the first portion having a length such that the first portion terminates in at least one of the kidney and ureter of the patient, the second portion of the elongate member configured to deliver fluid from a first location of the second portion to a second location of the second portion via at least one of capillary action and wicking, the second portion of the elongate member configured to be disposed within at least one of a bladder of a patient and the ureter of the patient. This stent may be modified to demonstrate managed degradation according to the present disclosure.

In another embodiment, the stent contains at least one filament, where this filament has a longitudinal axis and is formed from materials including a bioabsorbable polymeric material. Polymer molecules within the bioabsorbable polymeric material may have a helical orientation which is aligned with respect to the longitudinal axis of the filament. The stent is at least partially bioabsorbed by a patient upon implantation or insertion of the stent into the patient. For example, the stent may comprise: a braided or woven configuration; a flared end portion at one of a proximal end or a distal end of the stent; and at least one filament having a longitudinal axis and comprising an oriented bioabsorbable polymeric material, wherein polymer molecules within the bioabsorbable polymeric material have a helical orientation which is aligned with respect to the longitudinal axis of the at least one filament. Optionally, one or more of the following may further describe the stent: the proximal end and the distal end comprise the flared end portion; the at least one filament is helically wound along at least a portion of a length of the stent; the stent comprises a plurality of the filaments, where optionally the plurality of the filaments are helically wound along at least a portion of a length of the stent, and where further optionally a first portion of the plurality of the filaments are helically wound in a first direction and a second portion of the plurality of the filaments are helically wound in an opposite direction to the first direction; the plurality of the filaments are braided and helically wound along at least a portion of the length of the stent; the stent comprises filaments of stainless steel or nitinol; the stent comprises between 12 and 36 helical filaments; where optionally between 6 and 18 filaments are in the form of helices, and are axially displaced in relation to each and wherein the helices extend in a first direction, and wherein an equal number of filaments comprise helices that extend a second direction that is opposite the first direction, the filaments are uniformly arranged about a longitudinal axis of the stent; the oriented bioabsorbable polymeric material comprises a single bioabsorbable polymer or a blend of bioabsorbable polymers; the oriented bioabsorbable polymeric material comprises a polymer selected from poly(α-hydroxy acid) homopolymers, poly(α-hydroxy acid) copolymers and blends thereof; the oriented bioabsorbable polymeric material comprises a polymer selected from polyglycolide, poly-L-lactide, poly-D-lactide, poly-DL-lactide, and blends thereof; the oriented bioabsorbable polymeric material has a crystallinity ranging from 0.1 to 20%; at least one filament comprises a core of the oriented bioabsorbable polymeric material; at least one filament comprises a coating of the oriented bioabsorbable polymeric material; the stent comprises a plurality of oriented filaments that are arranged to form a pattern of geometric diamond-shaped cells; a plurality of filaments are wrapped about one another to form interlocking joints; at least one filament comprises a therapeutic agent; and the stent is selected from a coronary vascular stent, a peripheral vascular stent, a urethral stent, a ureteral stent, a biliary stent, a tracheal stent, a gastrointestinal stent and an esophageal stent.

Another optional embodiment provides a stent which is a construct of a fiber-reinforced elastomeric film designed with at least one position-retaining end, wherein the fiber-reinforcement is a monofilament yarn or a combination with knitted or braided multifilament yarn, wherein the fiber-reinforced elastomeric film is in the form of a tube having at least one position-retaining end, wherein the retaining end is an inverted cone having a diameter at the wider cross-section exceeding that of the main tube and that can be reversibly compressed to conform with the main tube diameter, which is also smaller than that of the patient ureter, upon applying radial compressive force in an applicator. It is preferred that the inverted cone is partially slit, yielding a cone wall having at least two leaflets and preferably three to five leaflets to facilitate the radial compression upon insertion with an applicator.

Yet another optional embodiment provides a which is a construct of a fiber-reinforced elastomeric film designed with at least one position-retaining end wherein the fiber reinforcement is a combination of a monofilament and knitted or braided multifilament yarn, wherein the elastomeric film is tubular with a central main component having a smaller diameter than that of the patient ureter and with at least one position-retaining end wherein the position-retaining end is an asymmetrically inverted cone with a teardrop cross-section, slit axially, at the peak of the teardrop which has an average diameter at the wider cross-section exceeding that of the central main tube wherein the slit asymmetric cone can be reversibly compressed to conform with the central main tube diameter upon applying radial compressive force in an applicator.

In yet another optional embodiment, the stent is a construct of a fiber-reinforced elastomeric film, wherein the fiber-reinforcement is a monofilament yarn or a combination with knitted or braided multifilament yarn, wherein the reinforced elastomeric film is tubular with a central main component that is a unilaterally, longitudinally crimped, inflatable tube having a circular cross-section that is smaller than that of the patient ureter when outwardly expanded, and having at least one position-retaining end wherein the position-retaining end is a unilaterally crimped, inflatable, asymmetric, inverted cone having a teardrop cross-sectional geometry and a crimp at the peak of the teardrop that is collinear with the crimp of the central main tube, wherein the average diameter of the inverted cone, when outwardly expanded, exceeds that of the central main tube.

Optionally, the fiber-reinforced elastomeric film is formed of a segmented copolymer made from a polyethylene glycol and at least one cyclic monomer selected from the group represented by I-lactide, epsilon-caprolactone, trimethylene carbonate, glycolide, a morpholine-dione, p-dioxanone, and 1,5-dioxapan-2-one. Optionally, the film is formed from a mixture of epsilon-caprolactone and glycolide. Optionally, the film is formed from a mixture of L-lactide and glycolide. An exemplary composition of an elastomeric swellable film composition is a crystalline copolymer of a high molecular weight (20-35 kDa) polyethylene glycol (PEG) and 95/5 (molar) mixture of epsilon-caprolactone/glycolide, wherein the weight percent of the PEG component in the copolymer is about 10 percent.

Another exemplary composition of an elastomeric film composition is a crystalline segmented copolymer made in two steps. The first step entails the formation of an amorphous or low melting copolymer made from epsilon-caprolactone, trimethylene carbonate and glycolide by polymerization in the presence of triethanolamine and stannous octanoate as the initiator and catalyst, respectively. In the second step, the product of the first step is reacted with a mixture of I-lactide and epsilon-caprolactone to produce a crystalline triaxial final copolymer.

Optionally, a film may be prepared from electrospun fibers. Also optionally, a fiber-reinforced film may comprise or contain a monofilament yarn, optionally in combination with knitted or braided multifilament yarn, wherein the reinforcing monofilament yarn is formed of a segmented copolymer made from at least two cyclic monomers selected from the group represented by I-lactide, epsilon-caprolactone, trimethylene carbonate, glycolide, a morpholine-dione, p-dioxanone, and 1,5-dioxapan-2-one. Optionally, it is formed from I-lactide, epsilon-caprolactone, and trimethylene carbonate which is a relatively slowly degrading composition. Optionally, it is formed from glycolide, epsilon-caprolactone, and trimethylene carbonate which is a relatively quickly degrading composition.

The reinforcing monofilament yarn may also be a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of I-lactide, epsilon-caprolactone, trimethylene carbonate, glycolide, p-dioxanone, 1,5-dioxepan-2-one, and a morpholinedione. Furthermore, the reinforcing monofilament yarn can be a composite of an inorganic microparticulate dispersed phase of at least one material selected from the group consisting of barium sulfate, zirconium oxide, and absorbable phosphate glass and an absorbable polymeric matrix of a crystalline segmented copolymer of a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione.

In still yet another optional embodiment, the present disclosure provides a bioabsorbable and disintegratable, multicomponent endoureteral stent which is a construct of a fiber-reinforced elastomeric film designed with at least one position-retaining end, wherein the fiber-reinforcement is a monofilament yarn or a combination with knitted multifilament or braided yarn, wherein the reinforcing knitted or braided multifilament fabric is formed of a crystalline segmented copolymer. An exemplary composition of such copolymer is a triaxial copolymer made in two steps. The first step entails the formation of an amorphous or low melting triaxial prepolymer using epsilon-caprolactone and/or trimethylene carbonate in the presence of trimethylolpropane and stannous octanoate as the initiator and catalyst, respectively. In the second step, the product of the first step is reacted with glycolide or a mixture of glycolide with epsilon-caprolactone and/or trimethylene carbonate. Another exemplary composition is a copolymer for use in producing knitted or braided multifilament yarn, which is a crystalline copolymer made from a polyethylene glycol and at least one cyclic monomer selected from the group represented by I-lactide, ε-caprolactone; trimethylene carbonate, glycolide, a morpholine-dione, p-dioxanone, and 1,5-dioxapan-2-one, but preferably from a polyethylene glycol, I-lactide, and trimethylene carbonate, and more preferably from a segmented copolymer of I-lactide and trimethylene carbonate. Optionally, the copolymer is made from glycolide and trimethylene carbonate, which provides a relative fast degradation profile for the yarn.

Thus, in one embodiment the present invention provides an absorbable and disintegratable, multicomponent endoureteral stent which is a construct of a fiber-reinforced elastomeric film designed with at least one position-retaining end, wherein the fiber-reinforcement is a combination of a monofilament coil and a braided multifilament yarn, and wherein the film is formed of a crystalline segmented copolymer made from a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione. The film may also be formed from a crystalline segmented copolymer made from I-lactide and at least one cyclic monomer selected from the group consisting of glycolide, ε-caprolactone, trimethylene carbonate, p-dioxanone and 1,5-dioxepan-2-one, and a morpholinedione.

In addition, the present disclosure provides an absorbable and disintegratable multicomponent endoureteral stent which is a construct of a fiber-reinforced elastomeric film designed with at least one position-retaining end, wherein the fiber-reinforcement is a combination of a monofilament coil and a braided multifilament yarn, and wherein the reinforcing monofilament yarn is formed of a crystalline segmented copolymer made from at least two cyclic monomers selected from the group consisting of I-lactide, ε-caprolactone, trimethylene carbonate, glycolide, a morpholinedione, p-dioxanone and 1,5-dioxepan-2-one. Alternatively, the reinforcing monofilament yarn is a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of I-lactide, ε-caprolactone, trimethylene carbonate, glycolide, p-dioxanone, 1,5-dioxepan-2-one, and a morpholinedione. The reinforcing monofilament yarn can also be a composite of an inorganic microparticulate dispersed phase of at least one material selected from the group of barium sulfate, zirconium oxide, and absorbable phosphate glass and an absorbable polymeric matrix of a crystalline segmented copolymer of a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione.

Thus the present disclosure also provides an optional embodiment which is an absorbable and disintegratable multicomponent endoureteral stent which is a construct of a fiber-reinforced elastomeric film designed with at least one position-retaining end, wherein the fiber-reinforcement is a combination of a monofilament coil and a braided multifilament yarn, and wherein the reinforcing braided multifilament fabric is formed of a crystalline segmented copolymer made from a polyethylene glycol and at least one cyclic monomer selected from the group consisting of I-lactide, trimethylene carbonate, ε-caprolactone, glycolide, p-dioxanone, a morpholinedione and 1,5 dioxepan-2-one. Alternatively, the reinforcing braided multifilament tube is formed from a crystalline segmented copolymer of I-lactide and at least one cyclic monomer selected from the group consisting of glycolide, ε-caprolactone, trimethylene carbonate, p-dioxanone, 1,5-dioxepan-2-one, and a morpholinedione.

In another embodiment, the present disclosure provides that the stent is a construct of a fiber-reinforced elastomeric film designed with at least one position-retaining end, wherein the fiber-reinforcement is a tube of a braided or weft-knitted monofilament yarn, and wherein the fiber-reinforced film is tubular with a central main component having a smaller diameter than that of the patient ureter and having at least one position-retaining end, and wherein the position-retaining end is a highly flexible extension of the central main tube, acquiring a loop shape with an open end parallel to the axis of the central main tube after insertion in the patient ureter and the loop can be made co-linear with the central main tube during insertion with an applicator. The film component of the assembled stent is formed of a crystalline segmented copolymer made from a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione. Alternatively, the film is formed of a crystalline segmented copolymer made from I-lactide and at least one cyclic monomer selected from the group consisting of glycolide, ε-caprolactone, trimethylene carbonate, p-dioxanone and 1,5-dioxepan-2-one, and a morpholinedione.

In another embodiment, the present disclosure provides that the stent is a construct of a fiber-reinforced elastomeric film designed with at least one position-retaining end, wherein the fiber-reinforcement is a tube of a braided or weft-knitted monofilament yarn, and wherein the reinforcing braided or weft-knitted monofilament yarn is formed of a crystalline segmented copolymer made from at least two cyclic monomers selected from the group consisting of I-lactide, ε-caprolactone, trimethylene carbonate, glycolide, a morpholinedione, p-dioxanone and 1,5-dioxepan-2-one. Alternatively, the reinforcing braided or weft-knitted monofilament yarn is formed of a crystalline segmented copolymer made from a polyethylene glycol and at least one cyclic monomer selected from the group consisting of I-lactide, trimethylene carbonate, ε-caprolactone, glycolide, p-dioxanone, a morpholinedione and 1,5 dioxepan-2-one. The reinforcing weft-knitted or braided monofilament can also be a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of I-lactide, ε-caprolactone, trimethylene carbonate, glycolide, p-dioxanone, 1,5-dioxepan-2-one, and a morpholinedione. Furthermore, the reinforcing weft-knitted or braided monofilament can be a composite of an inorganic microparticulate dispersed phase of at least one material selected from the group of barium sulfate, zirconium oxide, and absorbable phosphate glass and an absorbable polymeric matrix of a crystalline segmented copolymer of a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione.

Optionally, the stent is a construct of a fiber-reinforced elastomeric film designed with at least one position-retaining end, wherein the fiber reinforcement is a weft-knitted or braided monofilament scaffold and the reinforced construct therefrom is in the form of a tube comprising a central main component having a diameter smaller than that of the patient ureter and at least one position-retaining end, wherein the position-retaining end is an inverted cone having a series of diameters designed to provide progressively wider cross-sections than that of the central main tube and can be reversibly compressed to conform radially with the central main tube upon applying radial compressive force during insertion to the urogenital tract using a tubular applicator, and wherein the film is formed of a crystalline segmented copolymer made from a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione. Alternatively, the film is formed of a crystalline segmented copolymer made from I-lactide and at least one cyclic monomer selected from the group consisting of glycolide, ε-caprolactone, trimethylene carbonate, p-dioxanone and 1,5-dioxepan-2-one, and a morpholinedione. The reinforcing weft-knitted or braided monofilament yarn may optionally be formed of a crystalline segmented copolymer made from at least two cyclic monomers selected from the group consisting of l-lactide, ε-caprolactone, trimethylene carbonate, glycolide, a morpholinedione, p-dioxanone and 1,5-dioxepan-2-one. Alternatively, the reinforcing braided or weft-knitted monofilament yarn is formed of a crystalline segmented copolymer made from a polyethylene glycol and at least one cyclic monomer selected from the group consisting of l-lactide, trimethylene carbonate, ε-caprolactone, glycolide, p-dioxanone, a morpholinedione and 1,5 dioxepan-2-one.

In another optional embodiment, the stent is a construct of a fiber-reinforced elastomeric film designed with at least one position-retaining end, wherein the fiber reinforcement is a weft-knitted or braided monofilament scaffold and the reinforced construct therefrom is in the form of a tube comprising a central main component having a diameter smaller than that of the patient ureter and at least one position-retaining end, wherein the position-retaining end is an inverted cone having a series of diameters designed to provide progressively wider cross-sections than that of the central main tube and can be reversibly compressed to conform radially with the central main tube upon applying radial compressive force during insertion to the urinogenital tract using a tubular applicator, and wherein the reinforcing weft-knitted or braided monofilament yarn is a composite of an inorganic microparticulate dispersed phase of at least one material selected from the group of barium sulfate, zirconium oxide, and absorbable phosphate glass and an absorbable polymeric matrix of a crystalline segmented copolymer made from at least two cyclic monomers selected from the group consisting of l-lactide, ε-caprolactone, trimethylene carbonate, glycolide, p-dioxanone, 1,5-dioxepan-2-one, and a morpholinedione. Alternatively, the reinforcing braid or weft-knitted monofilament yarn is a composite of an inorganic microparticulate dispersed phase of at least one material selected from the group of barium sulfate, zirconium oxide, and absorbable phosphate glass, and wherein an absorbable polymeric matrix of a crystalline segmented copolymer of a polyethylene glycol and at least one cyclic monomer selected from the group consisting of l-lactide, ε-caprolactone, trimethylene carbonate, glycolide, p-dioxanone, 1,5-dioxepan-2-one, and a morpholinedione.

In another embodiment, the present disclosure provides an absorbable and disintegratable, multicomponent endoureteral stent which is a construct of a fiber-reinforced elastomeric film designed with at least one position-retaining end, wherein the fiber reinforcement is a weft-knitted monofilament yarn and the reinforced construct is in the form of a tube with a central main component having a smaller diameter than that of the patient ureter and having at least one position-retaining end wherein the position-retaining end is a highly flexible extension of the central main tube, acquiring a loop shape with an open end parallel to the axis of the central main tube after insertion in the patient ureter and the loop can be made co-linear with the central main tube during insertion with an applicator, and wherein the film is formed of a crystalline segmented elastomeric high l-lactide copolymer and the monofilament is formed of a segmented l-lactide copolymer with at least one cyclic monomer selected from the group consisting of glycolide, ε-caprolactone and a morpholinedione, and wherein the monofilament contains a microparticulate inorganic filler selected from the group of barium sulfate, zirconium oxide, and an absorbable phosphate glass.

In one embodiment, the medical device is a stent comprising a filament which has a longitudinal axis and which comprises an oriented bioabsorbable polymeric material, wherein polymer molecules within the bioabsorbable polymeric material have a helical orientation which is aligned with respect to the longitudinal axis of the filament, and wherein the stent is at least partially bioabsorbed by a patient upon implantation or insertion of the stent into the patient. In optional embodiments, the following one or more features may further characterize the medical device: a) the filament is helically wound along at least a portion of the length of the stent; b) the stent comprises a plurality of said filaments, where optionally the plurality of filaments are helically wound along at least a portion of the length of the stent, optionally a plurality of the filaments are helically wound in a first direction and a plurality of the filaments are helically wound in an opposite direction; c) the filament is a braided filament; a plurality of the braided filaments are braided and helically wound along at least a portion of the length of the stent; d) the filament is a knitted filament; e) the plurality of filaments are knitted filaments; the orientated bioabsorbable polymeric material comprises either a single bioabsorbable polymer or a blend of bioabsorbable polymers; f) the oriented bioabsorbable polymeric material comprises a polymer selected from poly(alpha-hydroxy acid) homopolymers, poly(alpha-hydroxy acid) copolymers and blends thereof; g) the oriented bioabsorbable polymeric material comprises a polymer selected from polyglycolide, poly-L-lactide, poly-D-lactide, poly-DL-lactide, and blends thereof; h) the oriented bioabsorbable polymeric material has a crystallinity ranging from 0.1 to 20%; i) the filament comprises a core of oriented bioabsorbable polymeric material; j) the stent is selected from a coronary vascular stent, a peripheral vascular stent, a urethral stent, a ureteral stent, a biliary stent, a tracheal stent, a gastrointestinal stent and an esophageal stent.

Optionally, the stent is capable of maintaining patency and remaining at the application site for at least two days, or 2-3 weeks after implantation, or has degraded after 7 weeks of being at the implantation site, or has largely degraded after 90 days, or has entirely degraded by four months. Optionally, the medical device, e.g., a ureter stent, remains intact during at least the first 48 hours after being placed within the host. For the period of 7 days after implantation, the medical device is preferably capable of being repositioned or removed from the host as a single device. About 1 week after implantation, the medical device may start to create HIVS fragments, although in some patients it may take a little more or less time for fragmentation to occur. Typically, during weeks 2-3 after implantation, HIVS fragments are formed and become separated from the medical device, e.g., by excretion in the event that the medical device is a ureter stent. Fragmentation may continue for several more weeks, e.g., into weeks 4-6 after implantation. Optionally, the majority of the medical implant has been elimination from the patient by about 90 days (about 12-13 weeks) after placement. Some amount of the medical device may remain within the host for up to about 120 days.

The present disclosure provides the following additional exemplary embodiments:

In one embodiment, the medical device is a biodegradable endoureteral stent. The stent comprises a tubular elastomeric film and a tubular fiber reinforcement, where the tubular elastomeric film is a single tube covering the tubular fiber reinforcement. The stent optionally has at least one position-retaining end. The device has a central main tube having a smaller diameter than that of a patient ureter, wherein the at least one position-retaining end, if present, is an extension of the central main tube. The central main tube is a generally tubular structure, the generally tubular structure comprising a sidewall enclosing a lumen where a longitudinal axis runs along a length of the lumen from a distal end to a proximal end of the structure, the tubular structure further comprising a plurality of bands that each encircle the longitudinal axis and have a distal side and a proximal side, the plurality of bands comprising relatively high in vivo stability bands that are separated by relatively low in vivo stability bands. The stent is configured to be positioned in the patient ureter and extend from a patient kidney to a patient bladder and optionally to be retained in position by the at least one position-retaining end. In one construction, the film reinforces and impregnates the fiber-reinforcement, wherein the fiber-reinforcement comprises a monofilament coil disposed over a knitted or braided tube of a monofilament or multifilament yarn that together forms the sidewall that encloses the lumen of the generally tubular structure. The film and fiber reinforcement may each comprise an absorbable crystalline segmented copolymer comprising at least one cyclic monomer. The film and fiber reinforcement alone are capable of maintaining ureteral patency.

In one embodiment, the endoureteral stent of the present disclosure can be placed by inserting a cystoscope through the patient's urethra and into the patient's bladder. The clinician will use the cystoscope to locate the opening where the ureter connects to your bladder. The clinician will thread the endoureteral stent of the disclosure through the cystoscope and into the patient's ureter such that once a curl of the stent is in the patient's kidney and the other curl at the opposite end of the stent remains in the patient's bladder. After the stent has been placed, the cystoscope is removed.

As mentioned above, the biodegradable endoureteral stent of the present disclosure comprises a plurality of bands that each encircle the longitudinal axis and have a distal side and a proximal side, the plurality of bands comprising relatively high in vivo stability bands that are separated by relatively low in vivo stability bands. The generally tubular structure, which may also be referred to as the central main tube, may be designated as proximal end of the tube-(LIVS-HIVS)n-LIVS-distal end of the tube, or proximal end of the tube-(HIVS-LVS)n-HVS-distal end of the tube. In either case, n designates the number of repeating LIVS-HIVS units, and may be an integer of at least 1, up to about 100. Optionally, n is selected from 1, 2, 3, 4, 5, 6, 7, 8, 9, or 10. Optionally, n is selected from 2, 3, 4, 5, 6, 7, 8, 9, or 10. Optionally, n is selected from 3, 4, 5, 6, 7, 8, 9, or 10. Optionally, n is selected from 4, 5, 6, 7, 8, 9, or 10. In this embodiment, the tubular structure comprises alternating bands of relatively high in vivo stability and relatively low in vivo stability.

The following options may also further define the endoureteral stent of the present disclosure: a) the stent has at least one position retaining end, and that position-retaining end is a flexible extension of the central main tube, acquiring a goose-neck shape after insertion in the patient ureter but can be made colinear with the central main tube during insertion with an applicator; b) the tubular elastomeric film comprises a crystalline segmented copolymer of a polyethylene glycol and at least one cyclic monomer selected from the group consisting of l-lactide, epsilon-caprolactone, trimethylene carbonate, glycolide, p-dioxanone, 1,5-dioxepan-2-one, and a morpholinedione; c) the tubular elastomeric film comprises a crystalline segmented copolymer of I-lactide and at least one cyclic monomer selected from the group consisting of glycolide, ε-caprolactone, trimethylene carbonate, p-dioxanone and 1,5-dioxepan-2-one; d) the monofilament coil comprises a crystalline segmented copolymer of at least two cyclic monomers selected from the group consisting of I-lactide, ε-caprolactone, trimethylene carbonate, glycolide, a morpholinedione, p-dioxanone and 1,5-dioxepan-2-one; e) the monofilament coil comprises a composite comprising a polymeric matrix and an inorganic microparticulate dispersed phase contained within the matrix, the matrix comprising a crystalline segmented copolymer and the inorganic microparticulate dispersed phase comprising at least one material selected from the group consisting of barium sulfate, zirconium oxide, and absorbable phosphate glass; f) the monofilament coil comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; g) the monofilament coil comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione; h) the fiber-reinforcement comprises a monofilament coil and a braided tube of a multifilament yarn, where optionally, 1) the tubular elastomeric film comprises a crystalline segmented copolymer of polyethylene glycol and at least one cyclic monomer selected from the group consisting of I-lactide, ε-caprolactone, trimethylene carbonate, glycolide, p-dioxanone, 1,5-dioxepan-2-one, and a morpholinedione; 2) the tubular elastomeric film comprises a crystalline segmented copolymer of I-lactone and at least one cyclic monomer selected from the group consisting of glycolide, ε-caprolactone, trimethylene carbonate, p-dioxanone, and 1,5-dioxepan-2-one, and a morpholinedione; 3) the monofilament coil comprises a crystalline segmented copolymer of at least two cyclic monomers selected from the group consisting of I-lactide, epsilon-caprolactone, trimethylene carbonate, glycolide, a morpholinedione, p-dioxanone, 1,5-dioxepan-2-one; 4) the monofilament coil comprises a composite comprising a polymeric matrix and an inorganic microparticulate dispersed phase contained within the matrix, the matrix comprising a crystalline segmented copolymer of at least two cyclic monomers selected from the group consisting of I-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; 5) the monofilament coil comprises a composite comprising a polymeric matrix and an inorganic microparticulate dispersed phase contained within the matrix, the matrix comprising a crystalline segmented copolymer of a polyethylene glycol and at least two cyclic monomer selected from the group consisting of I-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; 6) the multifilament yarn comprises a crystalline segmented copolymer of a polyethylene glycol and at least one cyclic monomer selected from the group consisting of I-lactide, trimethylene carbonate, ε-caprolactone, glycolide, p-dioxanone, a morpholinedione and 1,5-dioxepan-2-one; 7) the multifilament yarn comprises a crystalline segmented copolymer of I-lactide and at least one cyclic monomer selected from the group consisting of glycolide, ε-caprolactone, trimethylene carbonate, p-dioxanone, 1,5-dioxepan-2-one and a morpholinedione; j) the monofilament coil is disposed over a tube of weft-knitted monofilament yarn, where optionally 1) the tubular elastomeric film comprises a crystalline segmented copolymer of polyethylene glycol and at least one cyclic monomer selected from the group consisting of I-lactide, ε-caprolactone, trimethylene carbonate, glycolide, p-dioxanone, 1,5-dioxepan-2-one, and a morpholinedione; 2) the tubular elastomeric film comprises a crystalline segmented copolymer of I-lactide and at least one cyclic monomer selected from the group consisting of glycolide, ε-caprolactone, trimethylene carbonate, p-dioxanone and 1,5-dioxepan-2-one, and a morpholinedione; 3) the monofilament yarn comprises a crystalline segmented copolymer of at least two cyclic monomers selected from the group consisting of I-lactide, ε-caprolactone, trimethylene carbonate, glycolide, a morpholinedione, p-dioxanone, and 1,5-dioxepan-2-one; 4) the monofilament yarn comprises a crystalline segmented copolymer of a polyethylene glycol and at least one cyclic monomer selected from the group consisting of I-lactide, trimethylene carbonate, ε-caprolactone, glycolide, p-dioxanone, a morpholinedione, and 1,5-dioxepan-2-one; 5) the monofilament yarn comprises a composite comprising a polymeric matrix and an inorganic microparticulate dispersed phase contained within the matrix, the matrix comprising a crystalline segmented copolymer of at least two cyclic monomers selected from the group consisting of I-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; and 6) the monofilament yarn comprises a composite comprising a polymeric matrix and an inorganic microparticulate dispersed phase contained within the matrix, the matrix comprising a crystalline segmented copolymer of a polyethylene glycol and at least one cyclic monomer selected from the group consisting of I-lactide, ε-caprolactone, trimethylene carbonate, glycolide, p-dioxanone, 1,5-dioxepan-2-one, and a morpholinedione and the inorganic microparticulate dispersed phase comprising at least one material selected from the group consisting of barium sulfate, zirconium oxide, and absorbable phosphate glass; k) the stent is capable of maintaining patency and remaining at an application site for at least two days; l) the stent is capable of maintaining patency and remaining at an application site for two to four months; and m) the at least one position-retaining end contains at least 4 percent by weight of at least one powdered radiopacifier selected from the group consisting of barium sulfate, zirconium oxide, and bismuth subcarbonate.

The following are some specific the embodiments of the present disclosure:
1) A bioabsorbable implantable medical device comprising a generally tubular structure, the generally tubular structure comprising a sidewall enclosing a lumen where a longitudinal axis runs along a length of the lumen from a distal end to a proximal end of the structure, the tubular structure further comprising a plurality of bands that each encircle the longitudinal axis and have a distal side and a proximal side, the plurality of bands comprising relatively high in vivo stability bands that are separated by relatively low in vivo stability bands.
2) The medical device of embodiment 1 wherein the structure has at least one, or exactly one, band of relatively high in vivo stability and also has at least two, or exactly two, bands of relatively low in vivo stability.
3) The medical device of embodiment 1 wherein the structure has at least two, or exactly two, bands of relatively high in vivo stability and also has at least three, or exactly three, bands of relatively low in vivo stability.
4) The medical device of embodiment 1 wherein the structure has at least three, or exactly three, bands of relatively high in vivo stability and also has at least four, or exactly four, bands of relatively low in vivo stability.
5) The medical device of embodiment 1 wherein at least two bands of relatively high in vivo stability each have a length of 1-6 cm and are separated by one band of relatively low in vivo stability having a length of less than 1 cm.
6) The medical device of embodiment 1 wherein at least two bands of relatively high in vivo stability each have a length of 2-6 cm and are separated by one band of relatively low in vivo stability having a length of less than 1 cm.
7) The medical device of embodiment 1 wherein at least two bands of relatively high in vivo stability each have a length of 3-6 cm and are separated by one band of relatively low in vivo stability having a length of less than 1 cm.
8) The medical device of embodiment 1 wherein at least three bands of relatively high in vivo stability each have a length 3-6 cm and are separated by two bands of relatively low in vivo stability having a length of less than 1 cm.
9) The medical device of embodiment 1 wherein at least four bands of relatively high in vivo stability each have a length 3-6 cm and are separated by three bands of relatively low in vivo stability having a length of less than 1 cm.
10) The medical device of embodiment 1 wherein at least three bands of relatively high in vivo stability each have a length of 2-5 cm and are separated by two bands of relatively low in vivo stability having a length of less than 1 cm.
11) The medical device of embodiment 1 wherein at least three bands of relatively high in vivo stability each have a length of 3-6 cm and are separated by two bands of relatively low in vivo stability having a length of less than 1 cm.
12) The medical device of embodiment 1 wherein the tubular structure comprises alternating bands of relatively high in vivo stability and relatively low in vivo stability.
13) The medical device of embodiment 1 wherein the tubular structure comprises at least two bands of relatively high in vivo stability that are separated by one band of relatively low in vivo stability, and where the band of relatively low in vivo stability degrades at least twice as quickly in vivo as compared to the at least one band of relatively high in vivo stability.
14) The medical device of embodiment 1 wherein the tubular structure comprises at least two bands of relatively high in vivo stability that are separated by one band of relatively low in vivo stability, and the at least two bands of relatively high in vivo stability have essentially identical in vivo stability.

15) The medical device of embodiment 1 wherein the tubular structure comprises a band of relatively low in vivo stability located on each side of one band of relatively high in vivo stability, and the two bands of relatively low in vivo stability have non-identical in vivo stabilities.

16) The medical device of embodiment 1 wherein the tubular structure comprises a first band of relatively low in vivo stability that is located on a distal side of a first band of relatively high in vivo stability, and a second band of relatively low in vivo stability is located on a proximal side of the first band of relatively high in vivo stability, and the first band of relatively low in vivo stability has greater in vivo stability than does the second band of relatively in vivo stability.

17) The medical device of embodiment 1 wherein the tubular structure comprises a plurality of bands that have essentially identical relatively high in vivo stability.

18) The medical device of embodiment 1 wherein the tubular structure comprises a plurality of relatively low in vivo stability bands extending from a distal end to a proximal end of the structure and separated by bands of relatively high in vivo stability, wherein the in vivo stability of the plurality of relatively low in vivo stability bands increases from the distal end to the proximal end of the structure.

19) The medical device of embodiment 1 wherein the tubular structure is a mesh tube, or comprises a mesh tube.

20) The medical device of any of embodiments 1-19 wherein the tubular structure has a length of 10-30 cm.

21) The medical device of any of embodiments 1-20 wherein the sidewall comprises a monofilament coil encircling the lumen, a mesh that overlays the monofilament coil, and a coating deposited on the coil and the mesh.

22) The medical device of any of embodiments 1-21 further comprising a kidney-retaining structure at the proximal end of the device and a bladder-retaining structure at the distal end of the device.

23) The medical device of any of embodiments 1-22 further comprising a kidney-retaining structure in a form of a curl at the proximal end of the device and a bladder-retaining structure in a form of a curl at the distal end of the device.

24) The medical device of any of embodiments 1-23 which is a ureteral stent.

25) The medical device of any of embodiments 1-24 comprising a coating on the exterior surface of the device, wherein the coating has an average thickness.

26) The medical device of any of embodiments 1-25 comprising a coating on the exterior surface of device, wherein the coating has non-uniform thickness across the entire device.

27) The medical device of any of embodiments 1-26 comprising a coating on the exterior surface of the device, wherein the proximal end of the device comprises more coating compared to the distal end of the device.

28) The medical device of any of embodiments 1-27 which is a ureteral stent having a kidney-retaining structure at the proximal end of the device and a bladder-retaining structure at the distal end of the device, the device comprising a coating on the exterior surface of the device, wherein the proximal end of the device comprises more coating compared to the distal end of the device.

29) The medical device of any of embodiments 1-28 which does not include a containment layer which restricts the movement of the HIVS bands that separate from the medical device during in vivo degradation.

30) A method of preparing a medical device comprising:
   a. providing a bioabsorbable medical device comprising a generally tubular structure with a lumen running down the middle of the generally tubular structure within a side wall of the generally tubular structure, the bioabsorbable medical devicer; and
   b. exposing bands of the generally tubular structure to an ex vivo degradation condition to create low in-vivo stability (LIVS) bands from the exposed bands, and not exposing bands that are adjacent to the exposed bands of the generally tubular structure to the same degradation conditions, thereby creating high in vivo stability (HIVS) bands that are adjacent to the LIVS bands.

31) A medical device prepared by a method comprising the method of embodiment 30.

32) The medical device of embodiment 31 wherein the generally tubular structure comprises polyester.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Any of the medical device embodiments disclosed herein may include a drug, e.g., a therapeutic agent, or a prophylactic agent, as part of the medical device.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

In the description, certain specific details are set forth to provide a thorough understanding of various disclosed embodiments. However, one skilled in the relevant art will recognize that embodiments may be practiced without one or more of these specific details, or with other methods, components, materials, etc.

The Examples and preparations provided below further illustrate and exemplify the medical devices of the present invention and methods of preparing such devices. It is to be understood that the scope of the present invention is not limited in any way by the scope of the following Examples and preparations. In fact, unless the context indicates otherwise, when a specific polymer is used in an Example, this polymer is exemplary only and may, according to the present invention, be replaced with an alternative polymer. Also, when degradation times and properties are exemplified, it is to be understood that these values are approximations, and that other values would be obtained using different starting materials. The starting materials and various reactants utilized or referenced in the examples may be obtained from commercial sources, or are readily prepared from commercially available organic compounds, using methods well-known to one skilled in the art. Thus, the following examples are illustrative of embodiments of the invention, and are not to be construed as a limitation thereon.

EXAMPLES

Example 1

Preparation of Coil

A 1-liter stainless steel kettle with a 3-neck glass lid equipped with an overhead mechanical stirring unit, vacuum adapter, and nitrogen inlet was set up. The kettle was evacuated to a pressure of about 0.5 mm Hg and then purged with nitrogen. The kettle was charged with 9.15 g of paxTMC-1, which was pre-dried by heating it to 220° C. paxTMC-1 was prepared by combining trimethylene carbonate (TMC) and trimethylolpropane (TMP) at a TMC: TMP molar ratio of 15:1, in the presence of a tin catalyst, stannous octanoate, with heating and stirring. Glycolide (313.8 g, 2.705 mol), ε-caprolactone (132.1 g, 1.159 mol) and a radiopacifier (245 g barium sulfate microparticles having a diameter of between 1 to 4 microns) were added to the reaction kettle. The kettle apparatus was lowered into an oil bath, and its contents are placed under vacuum at 40° C. for 1 hour, after which the system was purged with nitrogen. The temperature of the oil bath was increased to 95° C. and the kettle contents were mixed thoroughly using the overhead stirrer. After a homogenous fluid composition was attained, a 0.2 M toluene solution of stannous octanoate (2.576 mL, $5.152 \times 10^{-4}$ moles stannous octanoate) was added. The temperature of the oil bath was increased to 180° C. and the stirring was continued for as long as possible. After stirring is not possible (due to high viscosity), the reaction product was maintained at 180° C. for 7 hours.

The kettle was removed from the oil bath and was allowed to cool to room temperature. The kettle was then lowered into a cold bath to solidify the polymer. The solid polymer was removed from the kettle and ground up. The ground material was sieved to provide a powder. The sieved powder was transferred to a 2-liter pear shaped glass flask and was placed on a Büchi rotavap. Vacuum was applied and after obtaining a vacuum of 0.25 mm Hg, the flask was lowered into an oil bath. The temperature of the oil bath was increased to 40° C. After 2 hours at 40° C. the temperature of the oil bath temperature was increased to 80° C., and after 1 hour at 80° C. the temperature of the oil bath was increased to 110° C. The temperature of the oil bath was maintained at 110° C. for 4 hours. The vacuum was broken and the material was removed from the flask.

Example 2

Melt-Spinning and Properties of Radiopaque Monofilaments Using Polymer from Example 1

A single screw extruder with four zones was used to extrude the polymer from Example 1 into a monofilament. A 325 line per inch filter pack was used in the extruder. Zone 1 was maintained at 95° C., zone 2 was maintained at 175° C., zone 3 was maintained at 208° C., and zone 4/Spin Pack were maintained at 210° C. The metering pump was operated at 8 rpm while the take up roll was set at 40-60 rpm. The polymer from Example 1 was extruded using a 0.4 mm die. The collected monofilaments had diameters between 0.48 mm and 0.54 mm. The fiber was drawn at 4.5× in the first stage at 55° C. and 0.5× in the second stage at 70° C., resulting in a monofilament diameter of 0.25 mm to 0.30 mm. The free shrinkage was about 8.85% to 10.43% at 50° C. The fiber was relaxed one half the free shrinkage plus 2% at 70° C. The resulting fibers had a maximum load of about 10-13N and were dimensionally stable.

Example 3

Manufacture of a Coiled Scaffold (CS)

A radiopaque monofilament, as prepared in Example 2, was coiled in a helical manner around a 0.047" diameter Teflon cord. The monofilament was wrapped around the Teflon cord at 33 to 35 coils per inch to provide a coiled scaffold (CS) which is an exemplary generally tubular structure of the present disclosure.

Example 4

Synthesis and Characterization of a Triaxial, Segmented Glycolide Copolymer for Use in Preparing Knitted Scaffolds A reaction apparatus was assembled including a 1 L stainless steel kettle with a 3-neck glass lid equipped with an overhead mechanical stirring unit, vacuum adapter, and nitrogen inlet. A vacuum was applied to the reaction apparatus. After a vacuum of 0.5 mmHg was obtained, the apparatus was purged with nitrogen. An initial charge of paxTMC-1 (16.0 g, as described in Example 1), ε-caprolactone (38.6 g, 0.3382 moles), and glycolide (745.4 g, 6.4262 moles) were added to the kettle. The reaction apparatus was then lowered into an oil bath. The oil bath was then heated to 110° C. and the reaction mixture was mixed under positive nitrogen pressure. Once the polymeric initiator (pax-TMC) appeared to be thoroughly dissolved in the molten monomers, a solution of stannous octanoate (0.966 ml of a 0.2M stannous octanoate in toluene, $1.933\times10^{-4}$ moles) was added to the reaction mixture. The temperature of the oil bath was increased to 180° C. The reaction mixture was stirred until the mixture became too viscous to stir. The reaction was maintained at 180° C. for an additional 5 hours. The reaction vessel was removed from the oil bath and the polymer was cooled until it solidified. The cooled polymer was removed from the reaction kettle and was ground into a powder. The ground material was sieved. The sieved polymer was transferred to a 2 L pear shaped glass flask and placed on a Büchi rotavap. Vacuum was applied and after obtaining a vacuum of 0.5 mmHg, the flask was lowered into an oil bath. The temperature of the oil bath was increased to 40° C. After 2 hours at 40° C., the temperature of the oil bath was increased to 80° C. After 1 hour at 80° C., the temperature of the oil bath was increased to 110° C. Temperature of the oil bath was maintained at 110° C. for 4 hours. The vacuum was broken and the material was removed from the flask.

Example 5

Melt-spinning and Properties of Multifilament Yarn Using Polymer from Example 4

A single screw extruder with five zones was used to extrude the polymer from Example 4 into multifilament. A 400 line per inch filter pack was used in the extruder. Zone 1 was maintained at 190° C., zone 2 was maintained at 210° C., zone 3 was maintained at 222° C., zone 4/pump were maintained at 228° C., and zone 5/spin pack were maintained at 228° C. A 0.584 cc/rev Zenith metering pump was operated at 6.0 rpm while the denier control roll was set to a linear speed of 315 meters/minute. The fiber was then oriented over three high speed godets traveling at 200, 480, 480 M/minute and heated to 45° C., 80° C., and 26° C., respectively. The polymer from Example 4 was extruded using a 20 hole die with 0.018" diameter holes. The collected multifilament was then reoriented at speeds of 250 M/minute to 280 M/minute, and at a temperature of 100° C. The resulting fiber had a tenacity of about 3.26 and a denier of about 80.4.

Example 6

Preparation of a Knitted Scaffold (KS)

The 20 filament yarn from Example 5 was plied once to generate a 40 filament yarn. The multifilament yarn was weft knit in a continuous manner over the coiled scaffold of Example 3 using a lamb circular knitter. A ⅞" knitting cylinder with 12 course gauge needles was used to form the knitted scaffold over the coiled scaffold, where the resulting structure is an exemplary generally tubular structure of the present disclosure.

Example 7

Synthesis and Characterization of a Triaxial, Segmented L-Lactide Copolymer (P1)

A reaction apparatus was assembled including a 4 L stainless steel reactor equipped with an overhead mechanical stirring unit, a vacuum adapter, and a nitrogen inlet. A vacuum was applied to the reaction apparatus and after a vacuum of less than 0.5 mmHg was obtained, the apparatus was purged with nitrogen. The reaction temperature was controlled by circulating oil through the jacketed reactor. An initial charge of glycolide (254.9 g, 2.1976 moles), trimethylene carbonate (348.7 g, 3.4185 moles), pre-dried triethanolamine (3.0319 g, $2.0348\times10^{-2}$ moles), stannous octanoate (354.5 mg, $8.752\times10^{-4}$ moles), and ε-caprolactone (974.3 g, 8.5463 moles) was added a 2 L flask and dried under high vacuum for 1.25 hours at 40° C. The flask contents were then added to the 4 L reactor. The system was then purged with nitrogen. The temperature of the oil was increased to 175° C. and the contents mixed thoroughly for 6.5 hours. The temperature was then reduced to permit the addition of the final charge, of glycolide (226.6 g, 1.9534 moles) and L-Lactide (1195.5 g, 8.3021 moles). The temperature of the oil was then increased to 135° C. and maintained for 19 hours. The resulting polymer was removed from the vessel and dissolved at a concentration of 1 g per 4 milliliters dichloromethane (DCM). The polymer was precipitated by slowly adding the polymer/DCM solution to a sufficient volume of cold isopropyl alcohol that was being mechanically agitated. The precipitated polymer was isolated by vacuum filtration. The filtered polymer was then added to a sufficient volume of cold isopropyl alcohol that was being mechanically agitated. The polymer was then isolated by vacuum filtration. Once the majority of the solvent had been removed, the polymer was allowed to dry under vacuum to a constant weight.

Example 8

Assembling a Composite Ureteral Stent Construct

A polymer solution was prepared by combining 16.0 grams of polyethylene glycol (PEG 4600; $M_W$=4600), 1600 milliliters of acetone, and 144.0 grams of purified P1 (Example 7) in a glass jar. The glass jar was sealed with a lid. The jar was placed on a rolling mill like apparatus to continuously rotate the glass jar. The solution was rolled until the PEG 4600 and the P1 were fully dissolved in the acetone.

The dry, knitted scaffold from Example 6 was impregnated with the PEG 4600/P1 polymer solution described above using a continuous impregnating process that involved the continuous movement of the knitted core material through a 0.75-liter bath of polymer solution. The scaffold was unspooled and fed into a bath of coating solution, where two in-line submerged pulleys kept the scaffold material submerged for the length of the bath. As the impregnated material exited the bath, it passed through an air-circulating drying tube heated to 40° C., then through a stainless-steel element heated to 50° C., and then the impregnated material was spooled onto a final take-up spool. This coating process was repeated in order to provide a thicker coating of the PEG 4600/P1 coating on the scaffold.

The impregnated knitted scaffold was wrapped onto racks equipped with two parallel stainless steel bars of 0.5 inch diameter, which could be adjusted for separation distance to control final stent length. The newly-impregnated, knitted scaffold was wrapped onto these racks in a continuous fashion. The racks were annealed at 130° C. for 30 minutes. After the annealing process, the racks were allowed to cool to room temperature in a laminar flow hood.

Multiple stents were removed from each rack by cutting the scaffolding material at appropriate positions along interior positions of the separation rods of the shape-forming racks. These stents, which still contained the Teflon core, were modified by addition of a UVJ marker to each stent stem within one centimeter of what would ultimately become the proximal loop of each stent.

The proximal loops of the stents were given an additional coating by using an MTS Synergie (Model 100 and 200) testing apparatus to mechanically dip the proximal end of the stent into a coating solution in a controlled manner and using multiple cycles. The distal end of the stent was attached to the vertical fixture on the MTS testing apparatus, which is programmed to dip the stent into a 100 mL graduated cylinder containing 100 mL of the coating solution. The programmed procedure lowered the stent into the cylinder to the 20 mL marking and immediately raised the stent out of the cylinder. The MTS apparatus kept the stent above the coating solution for a time duration (about 30-300 seconds) sufficient to dry the coating such that the coating reached a non-tacky state. The dipping procedure was repeated, with the exception that the stent is lowered to the 40 mL marking. The MTS program performed two final dipping cycles, wherein the stent was lowered to the 60 mL and then to 80 mL mark respectively. This resulted in an exterior coating layer that has a thickness gradient, wherein the thickest layer of coating was located on the proximal loop. This ensured that the proximal loop was reinforced with more coating material than the rest of the stent so that the proximal loop does not degrade prematurely.

Stents were hung by distal loops in a laminar flow hood to dry. The TEFLON™ PTFE cores were removed from each stent by securing one end of the TEFLON core to position-fixed vise-grip pliers as the opposite end of the TEFLON is stretched using a second set of vise-grip pliers. A clean cut was made in the stretched TEFLON core at the secured end, and then the Teflon core of reduced diameter was pulled through the stent and discarded. Each stent was then trimmed to the appropriate specifications.

Example 9

Band Creation Using Base Treatment

A band that had lower in vivo stability as compared to the adjacent untreated portions of the stent, was prepared by placing the stent between two 5 mm×5 mm pieces of sponge. The sponges were clipped together to ensure that contact between the sponges and the stent was maintained circumferentially around the stent. Approximately 1 mL of a NaOH solution was then pipetted onto each sponge. The stent was then allowed to sit for 1 hour while in contact with the pieces of sponge. The sponges were then removed and the stent was rinsed with a deionized water for 15 seconds. The stents were then dried under vacuum. This process created one low in vivo stability (LIVS) band for each stent, where that LIVS band was located between two high in vivo stability (HIVS) bands of the stent.

This process was performed by treating stents with basic solutions having NaOH concentrations of either 0.5M, 0.75M, 1.0M, 1.25M or 3.0M to prepare the low in vivo stability bands. Each stent was treated with only one of these concentrations of base.

Example 10

Multiple Band Creation Using Base Treatment

Bands that had lower in vivo stability as compared to the adjacent untreated portions of the stent, were prepared by placing a stent between two 5 mm×5 mm pieces of sponge. The sponges were clipped together ensure that contact between the sponges and the stent was maintained circumferentially around the stent. A second set of sponges was attached in a similar manner to the stent with a distance of about 4 cm between the edges of the first set of sponges and the edges of the sponges of the second set. Approximately 1 mL of a NaOH solution was then pipetted onto each sponge. The stent was then allowed to sit for 1 hour In contact with the sets of sponges. The sponges were then removed and the stent was rinsed with a deionized water for 15 seconds. The stents were then dried under vacuum. A low in vivo stability (LIVS) band was created where each set of sponges was located. A HIVS band was thereby created between the two LIVS bands.

This process was performed by treating stents with basic solutions having NaOH concentrations of either 0.5M, 0.75M, 1.0M, 1.25M and 3.0M to prepare the low in vivo stability bands on different stents, i.e., each stent was treated with either 0.5M NaOH, 0.75M NaOH, etc. at each set of sponges.

Example 11

Multiple Band Creation Using Base Treatment—Gradient Creation

A gradient of bands that had progressively lower in vivo stability as compared to adjacent untreated portions of the stent, were prepared by placing a stent between two 5 mm×5 mm pieces of sponge. The sponge pieces were clipped together to ensure that contact between the sponges and the stent was maintained circumferentially around the stent. A second, third and fourth set of sponges were attached in a similar manner to the stent with a distance of about 4 cm between the edges of the sponges of one band to the edges of the sponges of the next nearest band. Approximately 1 mL of a 0.5 M NaOH solution was then pipetted onto each sponge of the set of sponges closest to the kidney retaining portion of the stent. Approximately 1 mL of a 0.75 M NaOH solution was then pipetted onto each sponge of the second set of sponges from the kidney retaining portion of the stent. Approximately 1 mL of a 1.0 M NaOH solution was then pipetted onto each sponge of the third set of sponges from the kidney retaining portion of the stent. Approximately 1 mL of a 1.25 M NaOH solution was then pipetted onto each sponge of the fourth set of sponges from the kidney retaining portion of the stent. The stent was then allowed to sit for 1 hour. The sponges were then removed and the stent was rinsed with a deionized water for 15 seconds. The stents were then dried under vacuum.

Example 12

Band Creation Using UV Light

A stent was placed in a holder that maintains the kidney curl and has an attachment point for insertion into a drill chuck. The holder was then inserted into the drill chuck and the chuck was tightened down to hold the stent. The body of the stent was then placed into the stainless steel stent band guide. The first band on the guide was 8 cm from the kidney curl. A 5 mm UV spot light was then placed into the guide hole where it was 0.8 mm from the surface of the stent. The guide allowed a 5 mm portion of the stent to be exposed to the UV light. A motor attached to the drill chuck was turned on so the stent rotated at 20 RPM. The UV unit was then turned on for a specific time so that the first band was irradiated with UV light. The light intensity was about 6

W/cm² and the irradiation time was varied from 3 seconds to 18 seconds. This process was then repeated for each band down the length of the stent. Bands were located 4 cm apart with an 8 cm "tail" on the kidney end of the stent. For a 24 cm stent, 4 UV treated (LIVS) bands were created on the stent and for a 30 cm long stent, 5 UV treated (LIVS) bands were created.

Example 13

Buckle Testing of the Treated Stents

Figure 8:
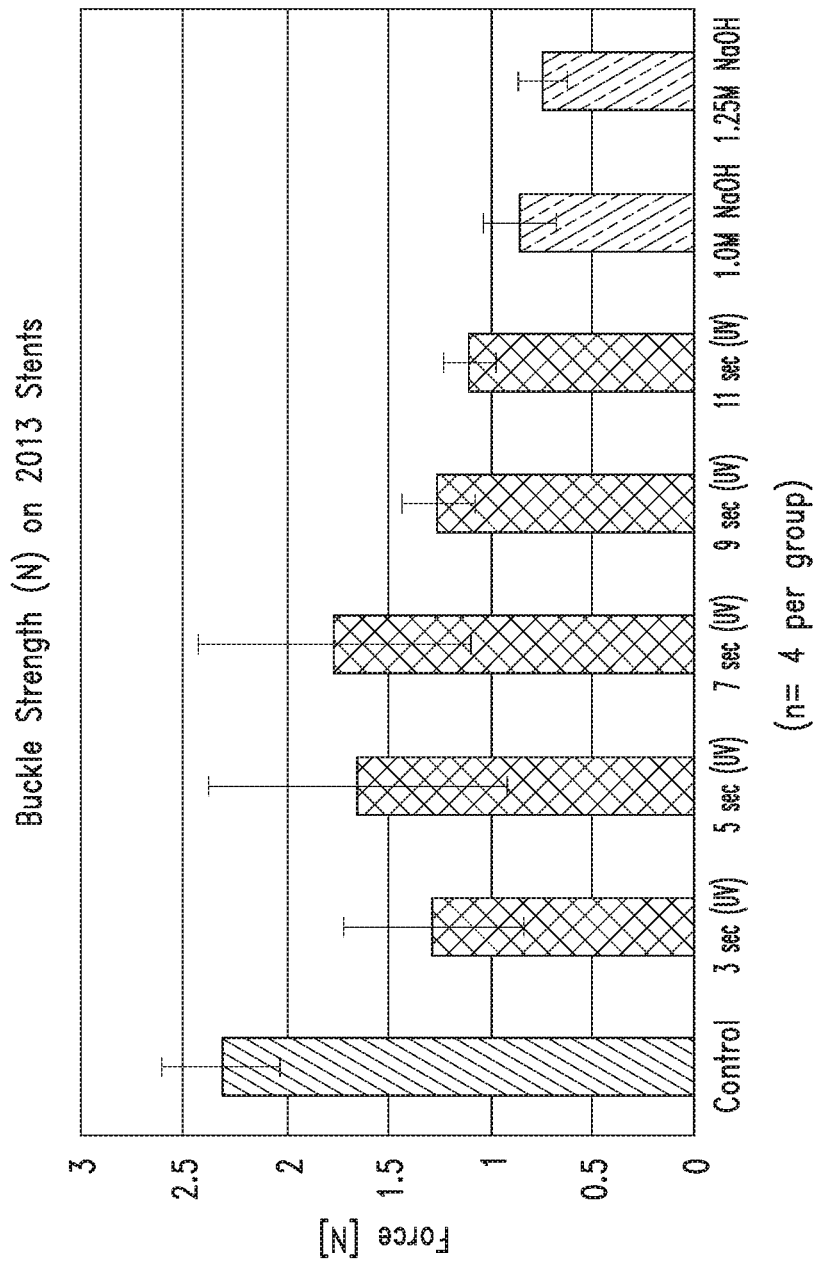
FIG. 8 is a graph showing buckle strength as a function of UV treatment and base treatment of a generally tubular structure.

A buckle test was used to determine the effect of the band creation process on the mechanical properties of the treated stent. A 4 cm length of stent that contained the treated area was used for the buckle test. The treated area was about in the middle of the sample (about 2 cm from each end). Two blocks with short cylinders (about 0.5 cm tall) attached in the center of each block were attached to a MTS instrument (measure force and movement, Model: MTS Synergie 100 and MTS Synergie 200) with one block attached to the base and one block to the load cell of the MTS instrument. The stent sample was placed so that it was held within these two cylinders when the gauge length of the MTS was set to 4 cm. The MTS was then turned on such that the stent sample was compressed as a function of time. The force required to buckle the stent sample was measured. The buckling of each stent sample occurred at the treatment site. The force data required to achieve buckling is shown in Table 1 and FIG. 8. The control sample was not treated to create a LIVS band.

TABLE 1

Summary of buckle force for tested samples.

| Treatment | Sample number | Peak load (N) | Avg | SD |
|---|---|---|---|---|
| Control | 1 | 2.01 | 2.31 | 0.29 |
|  | 2 | 2.34 |  |  |
|  | 3 | 2.58 |  |  |
| UV: 3 sec | 1 | 1.14 | 1.2775 | 0.44 |
|  | 2 | 0.95 |  |  |
|  | 3 | 1.92 |  |  |
|  | 4 | 1.1 |  |  |
| UV: 5 sec | 1 | 1.39 | 1.65 | 0.73 |
|  | 2 | 2.55 |  |  |
|  | 3 | 0.83 |  |  |
|  | 4 | 1.83 |  |  |
| UV: 7 sec | 1 | 1.81 | 1.7625 | 0.67 |
|  | 2 | 0.83 |  |  |
|  | 3 | 2.02 |  |  |
|  | 4 | 2.39 |  |  |
| UV: 9 sec | 1 | 1.34 | 1.255 | 0.17 |
|  | 2 | 1.01 |  |  |
|  | 3 | 1.41 |  |  |
|  | 4 | 1.26 |  |  |
| UV: 11 sec | 1 | 1.13 | 1.1 | 0.12 |
|  | 2 | 0.93 |  |  |
|  | 3 | 1.23 |  |  |
|  | 4 | 1.11 |  |  |
| NaOH: 1.0M | 1 | 0.76 | 0.8575 | 0.18 |
|  | 2 | 0.77 |  |  |
|  | 3 | 1.12 |  |  |
|  | 4 | 0.78 |  |  |
| NaOH: 1.25M | 1 | 0.86 | 0.7425 | 0.12 |
|  | 2 | 0.64 |  |  |
|  | 3 | 0.64 |  |  |
|  | 4 | 0.83 |  |  |

Example 14

Deflection Test of Treated Stents

Figure 9:
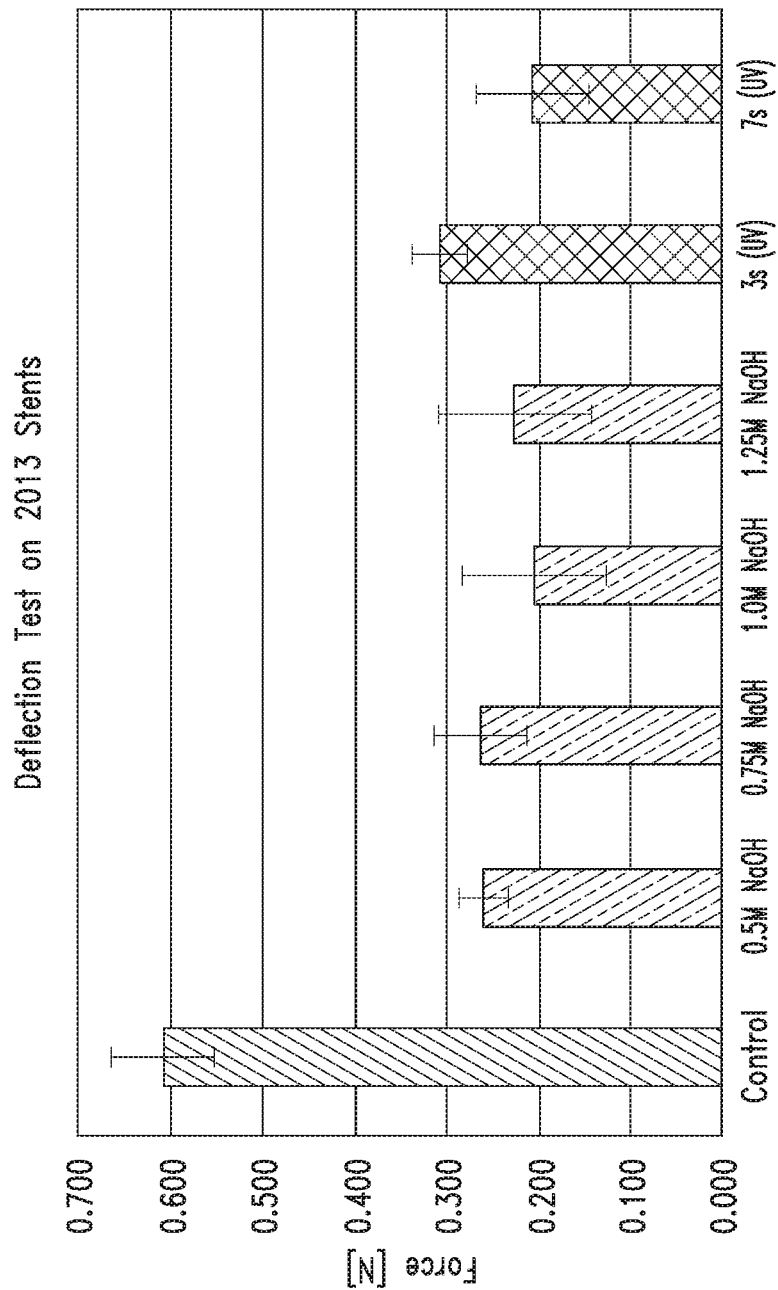
FIG. 9 is a graph showing the results of deflection testing on generally tubular structures as a function of UV treatment and base treatment.

A deflection test was used to measure the effect of LIVS bands on the strength of banded stents. A 4 cm long stent segment was used for this test. The stent segment was placed into a custom stainless steel fixture. This fixture was two blocks with guide pins that allowed the two halves to fit together tightly. There was a semicircle groove milled into the top and bottom of a block so when the two halves are put together it makes a continuous cylinder. The stent was placed into the bottom groove and then the top half was placed on the stent to firmly hold the stent without crushing it. The sample segment was placed so that the treatment site was right at the edge of the block to allow it to bend at the treatment site. Essentially there was 2 cm of the stent segment sticking out like a cantilever from the block. This block was placed on the base of the MTS instrument (measures force and movement, Model: MTS Synergie 100 and MTS Synergie 200) and the top of the three-point bend test fixture was put onto the load cell. The top half for the 3 point bend fixture was then used to press down on the portion of the stent that sticks out from the block and the force to "deflect" the stent was measured. The data obtained for the various treatments used to create the bands is shown in Table 2 and FIG. 9.

TABLE 2

Table of deflection data for treaded samples

|  | Control | NaOH: 0.5M | NaOH: 0.75M | NaOH: 1.0M | NaOH: 1.25M | UV: 3 s | UV: 7 s |
|---|---|---|---|---|---|---|---|
|  | 0.552 | 0.280 | 0.210 | 0.136 | 0.320 | 0.290 | 0.260 |
|  | 0.690 | 0.230 | 0.310 | 0.190 | 0.200 | 0.290 | 0.220 |
|  | 0.541 | 0.270 | 0.270 | 0.290 | 0.160 | 0.342 | 0.141 |
|  | 0.620 |  |  |  |  |  |  |
|  | 0.640 |  |  |  |  |  |  |
|  | 0.602 |  |  |  |  |  |  |
| Average | 0.608 | 0.260 | 0.263 | 0.205 | 0.227 | 0.307 | 0.207 |
| Std Dev | 0.056 | 0.026 | 0.050 | 0.078 | 0.083 | 0.030 | 0.061 |

Example 15

Tensile Strength Testing

Artificial urine was prepared by combining 50.0±1.0 g urea, 18.0±0.4 g NaCl, 5.0±0.1 g $Na_2HPO_4$, 15.0±0.3 g $KH_2PO_4$, 10.0±0.2 g $NH_4Cl$, 3.0±0.1 g $Na_2SO_3$, 4.0±0.1 g creatinine and 2 L deionized water.

Figure 10A:
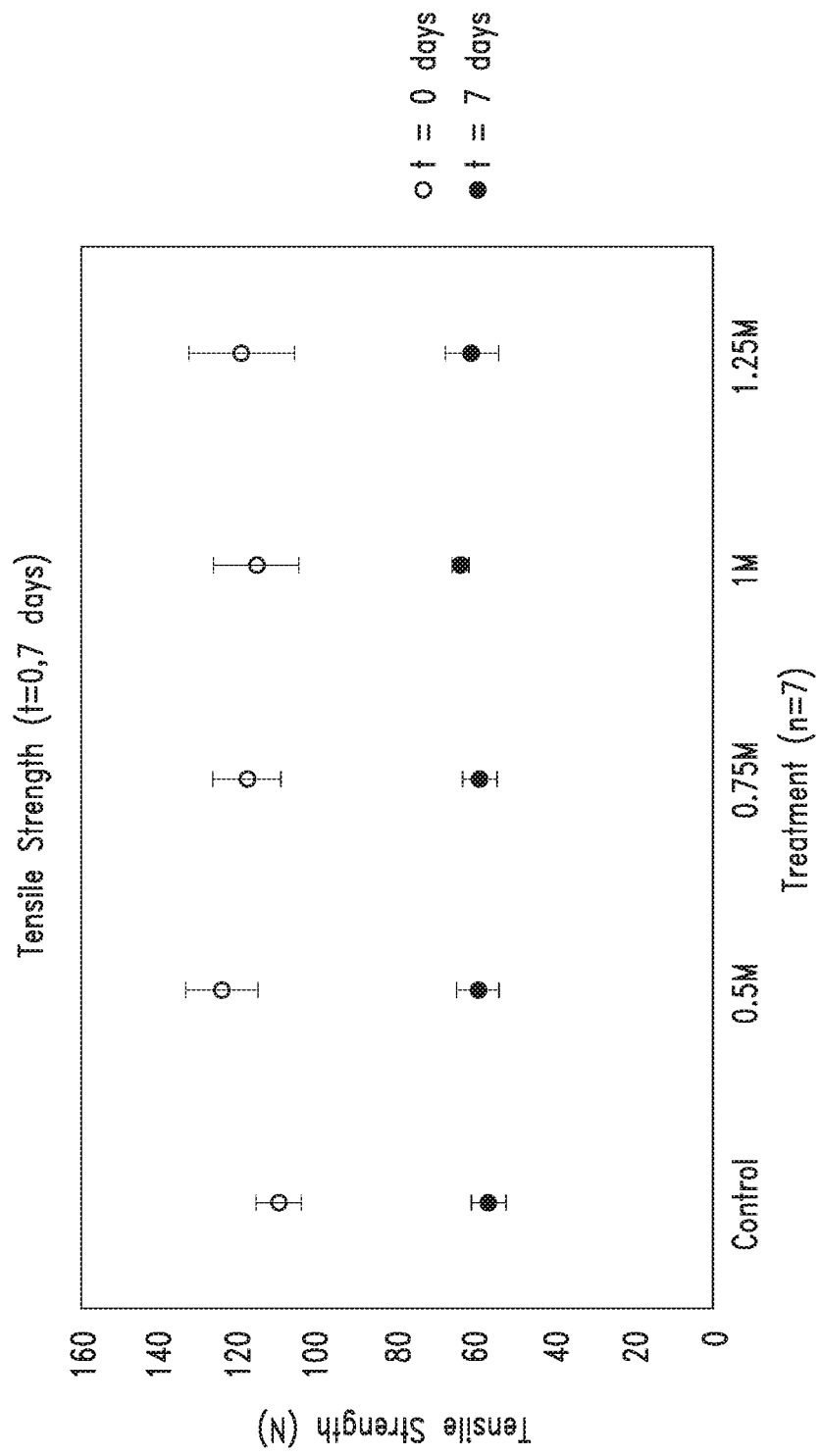
FIG. 10A is a graph showing the results of tensile strength testing on generally tubular structures as a function of degree of base treatment.
Figure 10B:
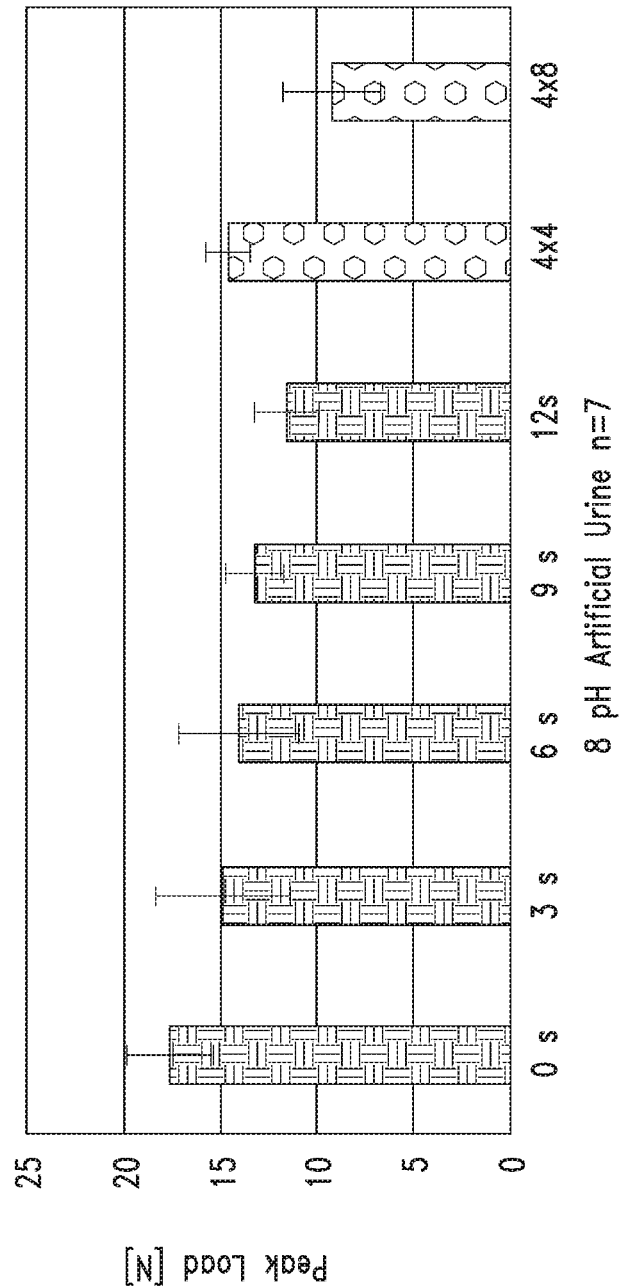
FIG. 10B is a graph showing the results of tensile strength testing on generally tubular structures as a function of UV treatment time.

Stents were tested at the site of the LIVS bands to determine the effect of each treatment strength on the stent mechanical integrity. Testing for base treated samples was conducted at 0 days and at 7 days post in vitro incubation in artificial urine pH 5.5-6.5 and 37° C. Testing for UV treated samples was performed on stent samples after aging for 5 days in pH 8 artificial urine. For tensile strength testing, segments of 5 cm sections of the stent were used as test specimens. Samples were loaded into the MTS (Model: MTS Synergie 100 and MTS Synergie 200) using vise grips. The tensile test was performed at a speed of 500 mm/min. The results are shown in FIG. 10A and FIG. 10B.

Example 16

In Vitro Testing of Fragmentation Patterns

Stents with LIVS and HIVS band sections were placed into a simulated use model developed to physiologically relevant criteria. The simulated use model comprised 3D-printed kidney and bladder components, a custom hydrogel ureter, and a custom hydrogel urethra. The system was placed in an oven set at 37° C. Stent samples were placed in the simulated use model and artificial urine was continuously circulated through the system. The artificial urine was replaced weekly. Stents were observed over time to determine their degradation/segmentation and migration behavior, as well as whether transient incontinence resulted during voiding. The end point of this study was defined as complete elimination of the stent.

For the base treated stents, no incontinence events for all final base treated stents (gradient applications of 0.5, 0.75, 1.0, and 1.25 M NaOH treatments) were observed, confirmed weight distribution targets to enable kidney curl relaxation and desired movement into bladder, all final stents saw segmentation at the treatment sites, segmentation allowed elimination without incontinence and final base treated stent kidney curls progressed into bladder by 28-35 days.

For UV treated stents, no incontinence events were observed. Incontinence events were classified as when the stent or stent fragments were stuck in the hydrogel urethra.

Example 17

Packaging of the Stent

In a largely or completely dust free environment, a stent was placed in a PET thermoformed tray. The thermoformed tray was closed and the tray with the stent was placed in a foil pouch. The foil pouch containing the stent was placed in a vacuum oven under vacuum at room temperature for a minimum of 14 hrs. The vacuum oven was then purged with nitrogen and the foil pouch containing the stent was then placed in a vacuum oven that was preheated to 40±2° C. The oven was closed and a vacuum (less than 5 Torr) was applied to the oven. The stent was maintained in the oven under vacuum for at least 24 hrs. The vacuum oven was then back flushed with dry nitrogen. The stent in the foil pouch was removed from the vacuum oven. The foil pouch was then heat sealed. For one set of samples a vacuum/nitrogen purge cycle was used to blanket the stent in a nitrogen atmosphere. A label was then applied to the outer surface of the foil pouch. The foil pouch was then sterilized using 24-40 kGy gamma radiation.

Example 18

Packaging of the Stent with Pusher

In a largely or entirely dust free environment, the stent was placed in a PET thermoformed tray. The thermoformed tray was closed and the tray with the stent was placed in a foil pouch. A stent pusher (New England Swaging Services) was placed in the foils pouch. The foil pouch containing the stent and pusher was placed in a vacuum oven under vacuum at room temperature for a minimum of 14 hrs. The vacuum oven was then purged with nitrogen and the foil pouch containing the stent was then placed in a vacuum oven that was preheated to 40±2° C. The oven was closed and a vacuum (less than 5 Torr) was applied to the oven. The stent was maintained in the oven under vacuum for at least 24 hrs. The vacuum oven was then back flushed with dry nitrogen. The stent/pusher in the foil pouch was removed from the vacuum oven. The foil pouch was then heat sealed. For one set of samples a vacuum/nitrogen purge cycle was used to blanket the stent in a nitrogen atmosphere. A label was then applied to the outer surface of the foil pouch. The foil pouch was then sterilized using 24-40 kGy gamma radiation.

Although any methods and materials similar or equivalent to those described herein can also be used in the practice or testing of the present invention, a limited number of the exemplary methods and materials are described herein. Generally, unless otherwise indicated, the materials for making the invention and/or its components may be selected from appropriate materials such as biodegradable polymers.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All publications and patents cited herein are incorporated herein by reference in their entirety for the purpose of describing and disclosing, for example, materials and methodologies described in the publications, which might be used in connection with the presently described invention. The present application incorporates by reference the disclosure of International Application No. PCT/US17/39130. The publications discussed above and throughout the text are provided solely for their disclosure prior to the filing date of the present application. Nothing herein is to be construed as an admission that the inventors are not entitled to antedate any referenced publication by virtue of prior invention.

What is claimed is:

1. A bioabsorbable implantable medical device comprising a generally tubular structure, the generally tubular structure comprising a monofilament in a shape of a coil, the coil comprising a sidewall enclosing a lumen where a longitudinal axis runs along a length of the lumen from a distal end to a proximal end of the structure, the monofilament coil consisting essentially of a bioabsorbable polymer, the coil comprising a plurality of bands that each encircle the longitudinal axis and have a distal side and a proximal side, the plurality of bands comprising relatively high in vivo stability bands that are separated by relatively low in vivo stability bands, and where the medical device is a graduated implant such that a proximal end of the medical device or portion thereof degrades more rapidly than does a distal end of the medical device due to a gradient in the properties of the low in vivo stability bands.

2. The medical device of claim 1 wherein the plurality of bands has at least three bands of relatively high in vivo stability and also has at least four bands of relatively low in vivo stability.

3. The medical device of claim 1 wherein the plurality of bands comprises alternating bands of relatively high in vivo stability and relatively low in vivo stability.

4. The medical device of claim 1 wherein the plurality of bands comprises at least two bands of relatively high in vivo stability that are separated by one band of relatively low in vivo stability, and where the band of relatively low in vivo stability degrades at least twice as quickly in vivo as compared to the at least one band of relatively high in vivo stability.

5. The medical device of claim 1 wherein the plurality of bands comprises a band of relatively low in vivo stability located on each side of one band of relatively high in vivo stability, and the two bands of relatively low in vivo stability have non-identical in vivo stabilities.

6. The medical device of claim 1 wherein the plurality of bands comprises a first band of relatively low in vivo stability that is located on a distal side of a first band of relatively high in vivo stability, and a second band of relatively low in vivo stability is located on a proximal side of the first band of relatively high in vivo stability, and the first band of relatively low in vivo stability has greater in vivo stability than does the second band of relatively low in vivo stability.

7. The medical device of claim 1 wherein the plurality of bands comprises a plurality of high in vivo stability bands that have essentially identical relatively high in vivo stability.

8. The medical device of claim 1 wherein the plurality of bands comprises a plurality of relatively low in vivo stability bands extending from a distal end to a proximal end of the structure and separated by bands of relatively high in vivo stability, wherein the in vivo stability of the plurality of relatively low in vivo stability bands increases from the distal end to the proximal end of the structure.

9. The medical device of claim 1 wherein the tubular structure comprises a mesh tube.

10. The medical device of claim 1 wherein the sidewall comprises a monofilament coil encircling the lumen, a mesh that overlays the monofilament coil, and a coating deposited on the coil and the mesh.

11. The medical device of claim 1 further comprising a kidney-retaining structure at the proximal end of the device and a bladder-retaining structure at the distal end of the device.

12. The medical device of claim 1 further comprising a kidney-retaining structure in a form of a curl at the proximal end of the device and a bladder-retaining structure in a form of a curl at the distal end of the device.

13. The medical device of claim 1 which is a ureteral stent.

14. The medical device of claim 1 further comprising a coating on the exterior surface of the device, wherein the coating has an average thickness.

15. The medical device of claim 1 further comprising a coating on the exterior surface of device, wherein the coating has non-uniform thickness across the entire device.

16. The medical device of claim 1 further comprising a coating on the exterior surface of the device, wherein the proximal end of the device comprises more coating compared to the distal end of the device.

17. The medical device of claim 1 which is a ureteral stent having a kidney-retaining structure at the proximal end of the device and a bladder-retaining structure at the distal end of the device, the device comprising a coating on the exterior surface of the device, wherein the proximal end of the device comprises more coating compared to the distal end of the device.

18. The medical device of claim 1 not including a containment layer which restricts the movement of the high in vivo stability bands that separate from the medical device during in vivo degradation.

19. The medical device of claim 1 wherein the bioabsorbable polymer is a poly(alpha-hydroxy acid) polymer or copolymer comprising the polymerization product of a monomer selected from glycolic acid or glycolide, lactic acid or lactide, hydroxybutyric acid, beta-hydroxypropionic acid, delta-valerolactone, and ε-caprolactone.

20. A method of preparing a medical device comprising: exposing a coil of a bioabsorbable medical device comprising a generally tubular structure with a lumen running down the middle of the generally tubular structure within a side wall of the generally tubular structure, the generally tubular structure comprising a monofilament in a shape of the coil, the coil comprising a sidewall enclosing a lumen where a longitudinal axis runs along a length of the lumen from a distal end to a proximal end of the structure, the monofilament coil consisting essentially of a bioabsorbable polymer, to ex vivo degradation condition to create low in vivo stability (LIVS) bands from the exposed bands, and not exposing bands that are adjacent to the exposed bands of the coil to the same degradation conditions, thereby creating high in vivo stability (HIVS) bands that are adjacent to the LIVS bands, and where the medical device is a graduated implant such that a proximal end of the medical device or portion thereof degrades more rapidly than does a distal end of the medical device due to a gradient in the properties of the low in vivo stability bands.

21. A medical device prepared by a method comprising the method of claim 20.

* * * * *